United States Patent
Ge et al.

(10) Patent No.: US 7,122,626 B2
(45) Date of Patent: *Oct. 17, 2006

(54) HALOGEN-SUBSTITUED THIENYL COMPOUNDS

(75) Inventors: Yigong Ge, So. San Francisco, CA (US); Matthew J. Taylor, San Francisco, CA (US); Eldon E. Baird, Half Moon Bay, CA (US); Roland W. Bürli, San Francisco, CA (US); Jacob A. Kaizerman, Redwood City, CA (US); Amanda E. Martin, San Francisco, CA (US); Brie Cadman, Napa, CA (US)

(73) Assignee: GeneSoft Pharmceuticals, Inc., South San Francisco, CA (US)

( * ) Notice: Subject to any disclaimer, the term of this patent is extended or adjusted under 35 U.S.C. 154(b) by 188 days.

This patent is subject to a terminal disclaimer.

(21) Appl. No.: 10/132,887

(22) Filed: Apr. 24, 2002

(65) Prior Publication Data

US 2003/0130198 A1 Jul. 10, 2003

Related U.S. Application Data

(60) Provisional application No. 60/286,454, filed on Apr. 26, 2001.

(51) Int. Cl.
*C07K 5/10* (2006.01)

(52) U.S. Cl. .................. 530/330; 530/329; 530/331; 549/29; 549/41

(58) Field of Classification Search ................ 530/329, 530/330, 331; 549/29, 41
See application file for complete search history.

(56) References Cited

U.S. PATENT DOCUMENTS

| | | | |
|---|---|---|---|
| 4,912,199 A | | 3/1990 | Lown et al. |
| 5,017,599 A | * | 5/1991 | Lazzari et al. ............... 514/422 |
| 5,049,579 A | | 9/1991 | Lazzari et al. |
| 5,310,752 A | * | 5/1994 | Lazzari et al. ............... 514/422 |
| 5,472,976 A | * | 12/1995 | Animati et al. ............. 514/422 |
| 5,502,068 A | * | 3/1996 | Lown et al. ................ 514/397 |
| 5,616,606 A | * | 4/1997 | Lown et al. ................ 514/422 |
| 5,698,674 A | * | 12/1997 | Bruice et al. ............... 530/331 |
| 5,753,629 A | * | 5/1998 | Beria et al. .................. 514/18 |
| 5,821,258 A | | 10/1998 | Matsunaga et al. |
| 5,852,011 A | | 12/1998 | Matsunaga et al. |
| 5,998,140 A | | 12/1999 | Dervan et al. |
| 6,090,947 A | | 7/2000 | Dervan et al. |
| 6,555,693 B1 | * | 4/2003 | Ge et al. ..................... 544/368 |
| 6,825,228 B1 | * | 11/2004 | Burli et al. ................. 514/422 |

FOREIGN PATENT DOCUMENTS

| | | |
|---|---|---|
| WO | WO 92/13838 A1 | 8/1992 |
| WO | WO 93/13739 A2 | 7/1993 |
| WO | WO 94/20463 A1 | 9/1994 |
| WO | WO 98/35702 A1 | 8/1998 |
| WO | WO 98/37066 A1 | 8/1998 |
| WO | WO 98/37067 A1 | 8/1998 |
| WO | WO 98/37087 A1 | 8/1998 |
| WO | WO 98/45284 A1 | 10/1998 |
| WO | WO 98/49142 A1 | 11/1998 |
| WO | WO 98/52614 A2 | 11/1998 |
| WO | WO 00/15209 A2 | 3/2000 |
| WO | WO 00/15773 A2 | 3/2000 |
| WO | WO 02/00650 A2 | 1/2002 |

OTHER PUBLICATIONS

Khalaf, Tetrahedron 56, 5225-39, 2000.*
Arcamone, F. et al., "Synthesis, DNA binding and antiviral activity of distamycin analogues containing different heterocyclic moieties." *Anti-Cancer Drug Design*, vol. 1, pp. 235-244 (1986).
Bailly, C. et al., "Sequence-specific DNA minor groove binders. Design and snythesis of netropsin and distamycin analogs." *Bioconjugate Chemistry*, vol. 9, No. 5, pp. 513-538 (1998).
Boger, D.L. et al., "Total synthesis of distamycin A and 2640 analogues: A solution-phase combinatorial approach to the discovery of new, bioactive DNA binding agents and development of a rapid, high-throughput screen for determining relative DNA binding affinity or DNA binding sequence selectivity." *Am. Chem. Soc.*, vol. 122, pp. 6382-6394 (2000).
Dyatkina, N.B. et al., "Minor groove DNA binders as antimicrobial agents. 1. Pyrrole tetraamides are potent antibacterials against vancomycin resistant *Enterococci* and methicillin resistant *Staphylococcus ureus*." *J.Med. Chem.*, vol. 45, pp. 805-817 (2002.
El-Naggar, A.M. et al, Synthesis of some 2-thenoyl-, 5-bromo-2-thenoyl- and 5-nitro-2-thenoylamino acid derivatives and their antimicrobial activity.: *J. Indian Chem. Soc.*, vol. 59, pp. 783-786 (1982).
Floreancig, P.E. et al., "Recognition of the minor groove of DNA by hairpin polyamides containing α-substituted-β-amino acids." *J. Am. Chem. Soc.*, vol. 122, pp. 6342-6350 (2000).

(Continued)

Primary Examiner—David Lukton
(74) Attorney, Agent, or Firm—Townsend and Townsend and Crew LLP

(57) ABSTRACT

Halogen substituted thienyl compounds exhibit potential as nucleic acid (especially double stranded DNA) binders and as antibiotic compounds. A representative thienyl compound has the structure

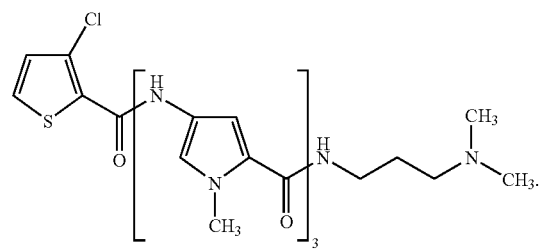

28 Claims, No Drawings

OTHER PUBLICATIONS

Khalaf, A.I. et al., "The synthesis of some head to head linked DNA minor groove binders." *Tetrahedron*, vol. 56, pp. 5225-5239 (2000).
Kopka, M.L. et al., "Defining GC-specificity in the minor groove: side-by-side binding of the di-imidazole lexitropsin to C-A-T-G-G-C-C-A-T-G." *Structure*, vol. 5, No. 8, pp. 1033-1046 (1997).
Matsumoto, T. et al., "Synthesis of halogenated oligo-*N*-methylpyrrolecarboxamide derivatives and their photochemical DNA cleaving activities." *Heterocycles*, vol. 34, No. 9, pp. 1697-1702 (1992).

Nielsen, P. "Sequence selective DNA recognition by synthetic ligands." *Bioconjugate Chemistry*, vol. 2, No. 1, pp. 1-12 (Jan./Feb. 1991).
Sakai, Y et al., "Synthesis of halogenated thiazole derivatives of oligo-*N*-methylpyrrole-carboxamide and their photochemical DNA cleaving activities." *Heterocycles*, vol. 36, No. 3, pp. 565-573 (1993).

* cited by examiner

SEQUENCE LISTING

<160> NUMBER OF SEQ ID NOS: 7

<210> SEQ ID NO 1
<211> LENGTH: 68
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotides with DNA target sites
<220> FEATURE:
<221> NAME/KEY: misc_binding
<222> LOCATION: (24)..(35)
<223> OTHER INFORMATION: DNA target site
<220> FEATURE:
<221> NAME/KEY: misc_binding
<222> LOCATION: (49)..(61)
<223> OTHER INFORMATION: DNA target site

<400> SEQUENCE: 1
ccgggaacgt agcgtaccgg tgcaaaaagc aaaaaggctc gacgccgcaa aaagacaaaa    60
aggctcga                                                            68

<210> SEQ ID NO 2
<211> LENGTH: 68
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotides with DNA target site complements
<220> FEATURE:
<221> NAME/KEY: misc_binding
<222> LOCATION: (12)..(24)
<223> OTHER INFORMATION: DNA target site complement
<220> FEATURE:
<221> NAME/KEY: misc_binding
<222> LOCATION: (38)..(49)
<223> OTHER INFORMATION: DNA target site complement

<400> SEQUENCE: 2
ggcgtcgagc cttttttgtct ttttgcggcg tcgagccttt ttgcttttttg caccggtacg    60 ctacgttc                                                            68

<210> SEQ ID NO 3
<211> LENGTH: 66
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotides with DNA target site
<220> FEATURE:
<221> NAME/KEY: misc_binding
<222> LOCATION: (7)..(20)
<223> OTHER INFORMATION: DNA target site

<400> SEQUENCE: 3
cgccgcaaaa agtacaaaaa ggctcgacgc cgcagctcgt cctagctagc gtcgtagcgt    60
cttaag                                                              66

```
<210> SEQ ID NO 4
<211> LENGTH: 66
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotides with DNA target site complement
<220> FEATURE:
<221> NAME/KEY: misc_binding
<222> LOCATION: (51)..(64)
<223> OTHER INFORMATION: DNA target site complement

<400> SEQUENCE: 4
tcgacttaag acgctacgac gctagctagg acgagctgcg gcgtcgagcc tttttgtact    60
ttttgc                                                               66

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence:DNA target
      site

<400> SEQUENCE: 5
aaaaagcaaa aa                                                        12

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence:DNA target
      site

<400> SEQUENCE: 6
aaaaagacaa aaa                                                       13

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence:DNA target
      site

<400> SEQUENCE: 7
aaaaagtaca aaaa                                                      14
```

HALOGEN-SUBSTITUED THIENYL COMPOUNDS

CROSS-REFERENCE TO RELATED APPLICATIONS

This application claims the benefit of U.S. Ser. No. 60/286,454, filed Apr. 26, 2001, the disclosure of which is incorporated herein by reference.

STATEMENT REGARDING FEDERALLY SPONSORED RESEARCH OR DEVELOPMENT

The United States government may have certain rights to this invention under DARPA Grant No. N65236-99-1-5427.

BACKGROUND OF THE INVENTION

1. Field of the Invention

This invention relates to halogen-substituted thienyl compounds, in particular ones binding to nucleic acids and having anti-microbial properties, and methods for their use.

2. Description of Related Art

A number of naturally occurring or synthetic compounds bind to double stranded nucleic acid, especially double stranded DNA ("dsDNA"). Some bind to the major groove, while others bind to the minor groove. Still others intercalate between adjacent base pairs. Combination binding modes are known, in which a compound has binding interactions with more than one nucleic acid site.

It has been proposed to use dsDNA binding compounds to regulate the expression of genes for medical purposes. If a disease is characterized by the overexpression or undesired expression of a gene (e.g., an oncogene), in principle the disease can be treated by suppressing wholly or partially the gene's expression via the binding of a compound to the gene or a promoter site thereof and interfering with transcription. Infections by pathogens such as fungi, bacteria, and viruses can be treated with compounds that affect the expression of genes essential for the pathogen's proliferation. Or, in a disease characterized by non- or under-expression of a beneficial gene, the expression of the beneficial gene can be up-regulated with a compound that binds to binding site of a repressor.

The natural products distamycin and netropsin represent a class of DNA-binding compounds that has been studied over the years:

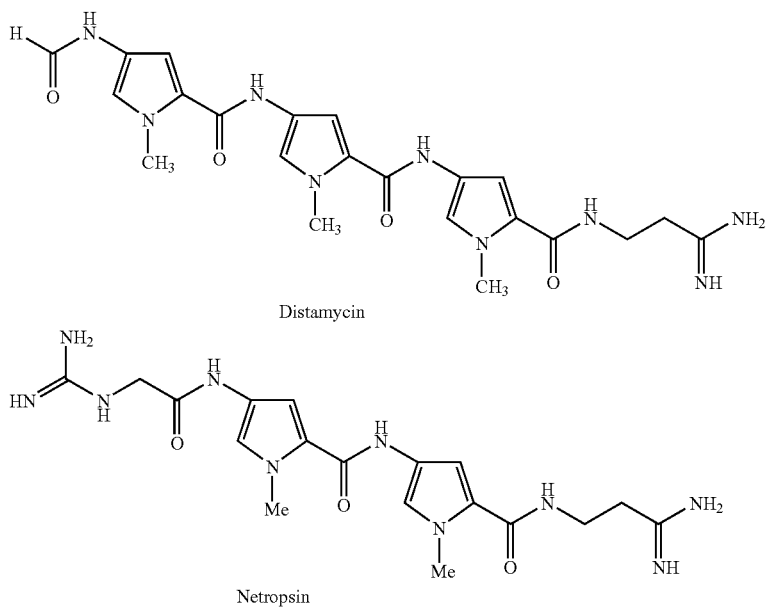

Distamycin

Netropsin

Distamycin and netropsin may be viewed as heteroaromatic polyamides, having as their core structural motif N-methylpyrrole carboxamide residues. They bind to the minor groove, their crescent molecular shapes providing a conformational fit within the groove. The binding occurs with a preference for A,T rich dsDNA tracts.

A number of heteroaromatic polyamides have been synthesized elaborating on the distamycin/netropsin motif, with the objective of enhancing or varying biological properties, increasing binding affinity to dsDNA, and/or improving specificity in base pair sequence recognition. The use of synthetic heteroaromatic polyamides in therapeutics has been proposed, for example, in Dervan et al., U.S. Pat. No. 5,998,140 (1999); Dervan et al., WO 00/15209 (2000); Dervan, WO 00/15773 (2000); and Gottesfeld et al., WO 98/35702 (1998). In many instances the structural variable investigated has been the heteroaromatic ring. Alternative heteroaromatic rings disclosed in the art include furan, imidazole, isoxazole, oxazole, pyrazole, pyridine, thiophene, and triazole rings.

Disclosures relating to heteroaromatic polyamides having thiophene rings include Arcamone et al., *Anti-Cancer Drug Design*, 1986, 1, 235–244; Nielsen, *Bioconjugate Chemistry*, January/February 1991, 2(1), p. 1; Bailly et al., *Bioconjugate Chemistry*, 1998, 9 (5), p. 513; Dickerson et al., *Structure*, 1997, 5, p. 1033; Khalaf et al., *Tetrahedron* 2000, 56, 5225–5239; Lown et al., U.S. Pat. No. 4,912,199 (1990); Lazzari et al., U.S. Pat. No. 5,017,599 (1991); Lazzari et al., U.S. Pat. No. 5,049,579 (1991); Lazzari et al., U.S. Pat. No.

5,310,752 (1994); Animati et al., U.S. Pat. No. 5,472,976 (1995); Lown et al., U.S. Pat. No. 5,502,068 (1996); U.S. Pat. No. 5,616,606 (1997); Bruice et al., U.S. Pat. No. 5,698,674 (1995); Beria et al., U.S. Pat. No. 5,753,629 (1998); Lown et al., WO 92/13838 (1992); and Animati et al., WO 94/20463 (1994). Matsumoto et al., *Heterocycles* 1992, 34, p. 1697, discloses halogenated oligo-N-methylpyrrole carboxamide derivatives, including those having halogenated thiophene groups. El-Naggar et al, *J. Indian Chem. Soc.*, 1982, LIX, p. 783, have reported on investigations on the anti-microbial properties of 5-bromo-2-thienyl carboxylic acid dipeptide derivatives.

BRIEF SUMMARY OF THE INVENTION

The present invention provides halogenated thienyl compounds useful as antibiotics and the pharmaceutically acceptable salts thereof, having a structure according to formula Ia:

(Ia)

wherein

Th is

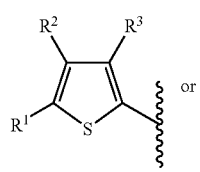
(IIa)

or

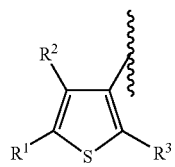
(IIb)

wherein each of $R^1$, $R^2$, and $R^3$ is H, F, Cl, Br, I, OH, $NO_2$, a substituted or unsubstituted ($C_1$–$C_{12}$)alkyl group, or a substituted or unsubstituted ($C_1$–$C_{12}$)heteroalkyl group; with the provisos that, when m is 3 or greater, at least one of $R^1$, $R^2$, and $R^3$ is F, Cl, Br or I (preferably F, Cl, or Br) and that, when m is 2, at least one of $R^2$ and $R^3$ is F, Cl, Br, or I, but $R^1$, $R^2$, and $R^3$ being otherwise independently variable. Preferably, when m equals 2, $R^1$ is other than F, Cl, Br, or I.

$D^1$ is selected from the group consisting of a chemical bond, a substituted or unsubstituted ($C_1$–$C_6$)alkylene group (e.g., —$CH_2$—, —$CH_2CH_2$—, —(C=O)—), —S(=O)—, and —S(=O)$_2$—. $D^1$ preferably is —C(=O)—, —$CH_2$—, —$CH_2CH_2$—, or —S(=O)$_2$—, most preferably —C(=O)—.

The subscript m is an integer ranging from 2 to 25, inclusive, preferably from 3 to 12, more preferably from 4 to 9, and most preferably from 3 to 5, inclusive.

Each Y is independently selected from the group consisting of:

(a) moieties $M^1$ having the formula

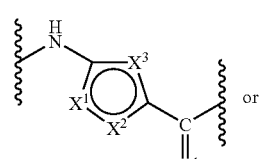
(IIIa)

or

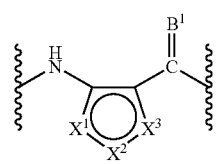
(IIIb)

wherein
each $B^1$ is independently selected from O, S, or NH;
one of $X_1$, $X_2$, and $X_3$ is a ring vertex selected from the group consisting of —O—, —S—, and —$NR^{10}$—, and the other two of $X_1$, $X_2$, and $X_3$ are ring vertices selected from the group consisting of =N— and =$CR^{11}$—;
each $R^{10}$ is independently H, a substituted or unsubstituted ($C_1$–$C_{12}$)alkyl group, or a substituted or unsubstituted ($C_1$–$C_{12}$)heteroalkyl group; and
each $R^{11}$ is independently H, Cl, F, Br, I, OH, $NO_2$, a substituted or unsubstituted ($C_1$–$C_{12}$)alkyl group, or a substituted or unsubstituted ($C_1$–$C_{12}$)heteroalkyl group;

(b) moieties $M^2$ having the formula

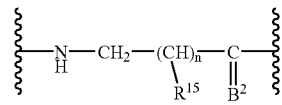
(IV)

wherein
n is 0 or 1;
each $B^2$ is independently O, S, or NH; and
each $R^{15}$ is independently H, OH, $NH^2$, or F; and (c) moieties $M^3$ having the formula

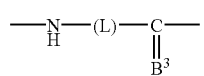
(V)

wherein
each $B^3$ is independently O, S, or NH and
each L is independently a divalent moiety separating —NH— and —(C=$B^3$)— by 3 or 4 atoms.

At least two Y's are moieties $M^1$.

$B^5(R^{20})_p$ is a terminal moiety, where $B^5$ is N or O; p is 1 if $B^5$ is O and 2 if $B^5$ is N; and each $R^{20}$ is independently H, a substituted or unsubstituted ($C_1$–$C_{12}$)alkyl group or a substituted or unsubstituted ($C_1$–$C_{12}$)heteroalkyl group. Preferably, $B^5$ is N and one $R^{20}$ is H.

At least one of $R^1$, $R^2$, $R^3$, $R^{10}$, $R^{11}$, and $R^{20}$ has at least one basic group having a $pK_b$ of 12 or less.

DETAILED DESCRIPTION OF THE INVENTION

Abbreviations and Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1-C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having six or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—OCH$_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1-C_4$)alkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR',—S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to hydrogen, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2$O$CH_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R''', —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, perfluoro($C_1$–$C_4$)alkoxy, and perfluoro($C_1$–$C_4$)alkyl, in a number ranging from zero to the total number of open valences on the aromatic ring system; and where R', R" and R''' are independently selected from hydrogen, ($C_1$–$C_8$)alkyl and heteroalkyl, unsubstituted aryl and heteroaryl, (unsubstituted aryl)-($C_1$–$C_4$)alkyl, and (unsubstituted aryl)oxy-($C_1$–$C_4$)alkyl.

Two of the substituents on adjacent atoms of the aryl or heteroaryl ring may optionally be replaced with a substituent of the formula -T-C(O)—($CH^2$)$_q$-U-, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -A-($CH_2$)$_r$-B-, wherein A and B are independently —$CH_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —($CH_2$)$_s$—X—($CH_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$–$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, ascorbic, propionic, isobutyric, maleic, malonic, lactic, malic, glutamic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (chiral centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

In the discussions below, reference is made to dsDNA as the nucleic acid, but it is to be understood that the invention is not limited to dsDNA and is applicable to other nucleic acids, i.e., ribonucleic acid.

Compounds

In formula Ia

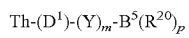
(Ia)

the preferred embodiment in which $D^1$ is carbonyl (—C(=O)—) results in Th being linked to Y via an amide (—C(=O)—NH—) linkage. Alternatively, $D^1$ can be, for example, alkylene (e.g., methylene, ethylene, or propylene), hydroxyethylene (—CH(OH)CH$_2$—); oxyethylene (—OCH$_2$CH$_2$—), aminoethylene (—NHCH$_2$CH$_2$—), aminomethylene (—NHCH$_2$—) and the like.

A preferred thienyl group Th is

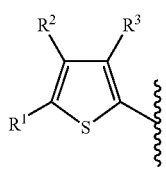
(IIa)

especially where $R^3$ is Cl. Preferred subcombinations in which $R^3$ equals Cl include (a) $R^1$ and $R^2$ are each H; (b) $R^1$ is H and $R^2$ is Br, and (c) $R^1$ is H and $R^2$ is CH$_3$.

A variety of synthetic methods can be used to connect Th with the remainder of the molecule. Several methods are cited here for illustrative purposes, as applied to distamycin analogs. An amine-terminated distamycin residue can be alkylated with an epoxide compound; see Arcamone et al., U.S. Pat. No. 4,738,980 (1988) and U.S. Pat. No. 4,766,142 (1988). Or, it can be sulfonylated with a sulfonic acid derivative; see Arcamone et al., *Anti-Cancer Drug Design*, 1986, 1, 235–244. Another approach is taught in Lazzari et al., U.S. Pat. No. 5,017,599 (1991); U.S. Pat. No. 5,049,579 (1991); and U.S. Pat. No. 5,310,752 (1994) and Animati et al., U.S. Pat. No. 5,670,534 (1997): condensation of an acyl compound with an amino-terminated distamycin residue in the presence of a condensing agent such as dicyclohexylcarbodiimide to form a carboxamide linkage. Animati et al., U.S. Pat. No. 5,412,9976 (1995) discloses the reaction of a carboxyimidate with an amine-terminated distamycin residue to form an amidine. The aforementioned patents are incorporated herein by reference.

Each moiety Y can be a moiety $M^1$, $M^2$, or $M^3$, characterized by an amino group at one open valence position and a carbonyl, thiocarbonyl, or imino at the other open valence position ($B^1$, $B^2$, and $B^3$ equals O, S, or NH, respectively). In the instance in which $B^1$, $B^2$, and $B^3$ are all equal to O, the resulting structure is a polyamide, with the various $M^1$, $M^2$, and $M^3$ being joined by amide linkages. In the alternative instance in which $B^1$, $B^2$, and $B^3$ are all equal to NH, the resulting structure is a polyamidine, with the various $M^1$, $M^2$, and $M^3$ being joined by amidine linkages (—C(=NH)—NH—). Lastly, in the instance in which $B^1$, $B^2$, and $B^3$ are all equal to S, the resulting structure is a polythioamide. Preferably, compound Ia is a polyamide.

Moieties $M^1$

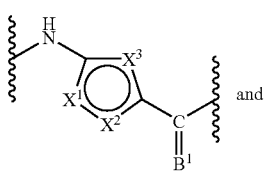
(IIIa)

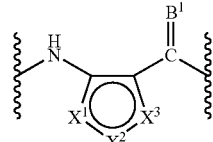
(IIIb)

are 5-membered ring heteroaromatic moieties, the selection of $X^1$, $X^2$, and $X^3$ determining the type of heteroaromatic ring. Exemplary heteroaromatic moieties include imidazole, pyrrole, pyrazole, furan, isothiazole, oxazole, isoxazole, thiazole, furazan, 1,2,3-thiadiazole, 1,2,4-thiadiazole, 1,2,5-thiadiazole, 1,3,4-thiadiazole, 1,2,3-triazole, 1,2,4-triazole, 1,3,4-oxadiazole, 1,2,4-oxadiazole, and thiophene moieties. At least two Y's in each compound Ia are moieties $M^1$.

The circle in the five-membered rings of IIIa and IIIb above is meant to indicate the presence of two double bonds, which, in some embodiments, can move within the ring.

Preferred moieties $M^1$ are IIIc (hereinafter "Py"), formally derived from 1-methyl-4-aminopyrrole-2-carboxylic acid, IIId (hereinafter "Hp"), formally derived from 1-methyl-3-hydroxy-4-aminopyrrole-2-carboxylic acid, and IIIe (hereinafter "Im"), formally derived from 1-methyl-4-aminoimidazole-2 carboxylic acid:

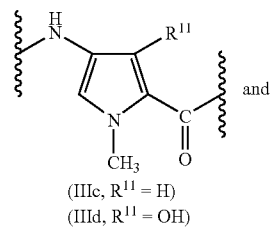
(IIIc, $R^{11}$ = H)
(IIId, $R^{11}$ = OH)

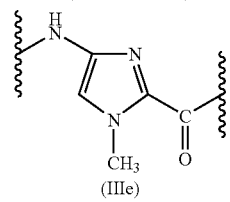
(IIIe)

Subsequent discussions in this specification will focus primarily on Py, Hp, and Im as the $M^1$ moieties, it being understood that this practice is illustrative and not limitative.

Different polyamide-dsDNA binding modes are known. In the simplest mode, often referred to as the 1:1 binding mode, a single polyamide molecule fits in the channel formed by the minor groove. In what is referred to as the 2:1 binding mode, two polyamide molecules fit side-by-side in the minor groove, preferably aligned in an antiparallel manner (i.e., with one polyamide being aligned N-to-C and the other polyamide being aligned C-to-N, where "C" and "N" refer to the carboxy and amino termini, respectively of the polyamides). Lastly, in what is referred to as a "hairpin" binding mode, a single polyamide molecule that has a more or less centrally positioned flexible moiety (i.e., a moiety $M^3$, as discussed in greater detail hereinbelow) folds around itself to adopt a hairpin conformation when it is bound to the minor groove, so that a first portion of the polyamide at one side of the hairpin turn is adjacent to a second portion of the polyamide at the other side of the hairpin turn.

In the 2:1 and hairpin binding modes, heteroaromatic moieties $M^1$ are positioned alongside each other, in a substantially face-to-face relationship. It has been shown by Dervan and co-workers (see above cited references) that, in these binding modes, heteroaromatic moiety pairs recognize specific dsDNA base pairs, giving rise to a set of "pairing rules" correlating heteroaromatic moiety pairs and the DNA base pairs they preferentially recognize. These pairing rules are summarized below:

| Heteroaromatic Pair | dsDNA Base Pair(s) Recognized |
|---|---|
| Im/Py | G/C |
| Py/Im | C/G |
| Py/Py | A/T, T/A (degenerate) |
| Hp/Py | T/A |
| Py/Hp | A/T |

Such recognition can give rise to dsDNA base pair sequence-specific binding by a heteroaromatic polyamide. The pairing rules enable the design of polyamides that target predetermined DNA base pair sequences, for example, a specific promoter site or a sequence characteristic of a gene.

Optionally, one or more moieties $M^2$

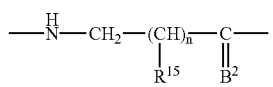

(IV)

can be present. A moiety $M^2$ can function as a "spacer" for adjusting the positioning of the heteroaromatic moieties $M^1$ relative to the dsDNA base pairs at the binding site. As a polyamide Ia binds in the minor groove, the alignment of heteroaromatic moieties $M^1$ with the DNA base pairs against which they are to be matched may drift as the number of heteroaromatic moieties $M^1$ increases. Alternatively, incorporation of a moiety $M^2$ adds flexibility to the polyamide, allowing its curvature to more accurately match that of the minor groove. The incorporation of one or more flexible moieties $M^2$ relaxes the curvature of the polyamide, permitting larger polyamides recognizing longer sequences of DNA. In some preferred embodiments a moiety $M^2$ is present for every 4 to 5 heteroaromatic moieties $M^1$, more preferably interrupting longer sequences of $M^1$ groups.

Preferred moieties $M^2$ are those corresponding to glycine (n=0 in formula IV, depicted as IVa below) and β-alanine (n=1 and $R^{15}$=H in formula IV; depicted as IVb below, hereinafter "β"), with the latter being especially preferred.

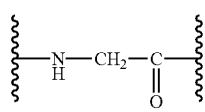

(IVa)

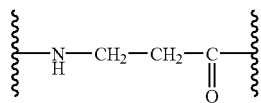

(IVb)

In some cases, a β-alanyl residue IVb can be substituted for a heteroaromatic moiety such as Im, Py, or Hp without loss of sequence specificity in binding to dsDNA.

Moieties $M^2$ in which h=1 and $R^{15}$=OH, $NH_2$, or F can be used to alter the binding affinity and specificity (relative to β-alanine), as disclosed in Floreancig et al., *J. Am. Chem. Soc.*, 2000, 122, 6342; the disclosure of which is incorporated herein by reference.

In moieties $M^3$ (formula V)

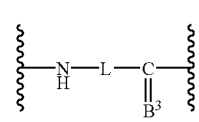

(V)

the group L provides a spacer of 3 to 4 atoms between —NH— and —C(=$B^3$)— and can be used to introduce a hairpin turn into a polyamide. Exemplary moieties $M^3$ include:

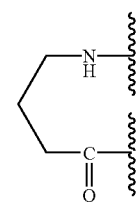

(Va)

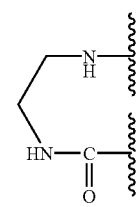

(Vb)

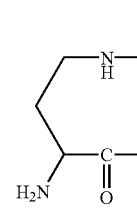

(Vc)

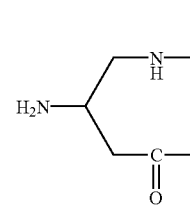

(Vd)

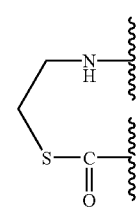

(Ve)

-continued

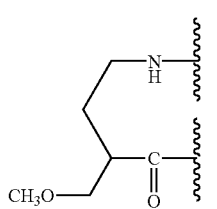 (Vf)

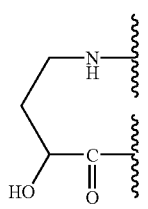 (Vg)

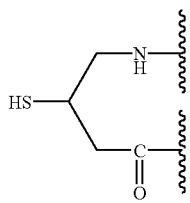 (Vh)

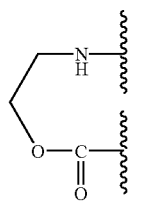 (Vi)

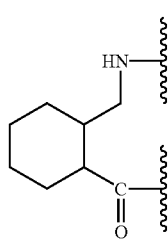 (Vj)

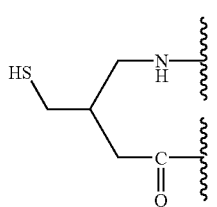 and (Vk)

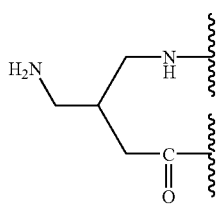 (Vl)

and their thiocarbonyl or imino analogs.

Moieties Va (hereinafter "γ"), corresponding to γ-aminobutyric acid, and Vc, corresponding to 2,4-diaminobutyric acid, are preferred. Selecting one enantiomer or the other of chiral moieties $M^3$ allows stereochemical control of the binding of polyamides to the minor groove, for example as disclosed in Baird et al., WO 98/45284 (1998) in respect of R-2,4-diaminobutyric acid and S-2,4-diaminobutyric acid (corresponding to R-Vc and S-Vc, respectively).

Yet another class of moieties $M^3$ is represented by the formula

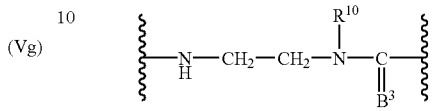

where $R^{10}$ and $B^3$ are as previously defined.

While the group L preferably provides a 3-atom separation between the —NH— and the —(C=$B^3$)—, a 4-atom separation is also permissible, as illustrated by a 5-aminovaleric acid residue (i.e., L equals —(CH$_2$)$_4$—):

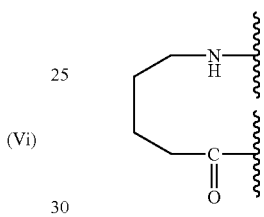

L can have pendant groups, which serve to enhance solubility or function as attachment points for other groups (e.g., Vc, Vd, Vg, Vh, Vk, Vl). The 3 to 4 atoms can be part of a larger group, which provides conformational rigidity (e.g., Vj). The 3 to 4 atoms can comprise carbon atoms only or it can include heteroatoms (e.g., Vb, Ve, Vi).

Polyamide compounds Ia can be synthesized by solid phase techniques from the corresponding amino acids or their derivatives, for instance IIIa', IIIb', and IIIc' for the synthesis of Py, Hp, and Im, respectively.

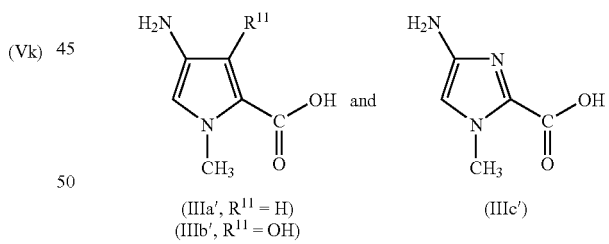

(IIIa', $R^{11}$ = H)
(IIIb', $R^{11}$ = OH)

(IIIc')

In solid phase synthesis, the polyamide is synthesized on a resin such as Boc-glycine-PAM-resin or Boc-β-alanine-PAM-resin, with moieties Y being added in series of steps involving amino-protected and carboxy-activated monomers, as taught in Dervan et al., U.S. Pat. No. 6,090,947 (2000); Baird et al., WO 98/37066 (1998); Baird et al., WO 98/37067 (1998); and Dervan et al., WO 98/49142 (1998); the disclosures of which are incorporated herein by reference.

$B^5(R^{20})_p$ is a terminal group, located at the end of the molecule distal from Th. Where moieties $M^1$, $M^2$, and $M^3$ represent amide moieties, it may be viewed as a C-terminal cap. In combination with the carbonyl group of a terminal $M^1$, $M^2$, and $M^3$ moiety, it can form an ester group ($B^5$ equals O) or an amide group ($B^5$ equals N). The two groups $R^{20}$ can be linked to each other to form a cyclic structure.

Preferably, $B^5$ is N and a $R^{20}$ contains a basic group, in particular an amine group. However, where a basic group is present elsewhere in the molecule, then $R^{20}$ need not contain a basic group. Examples of suitable groups $N(R^{20})_2$ include:

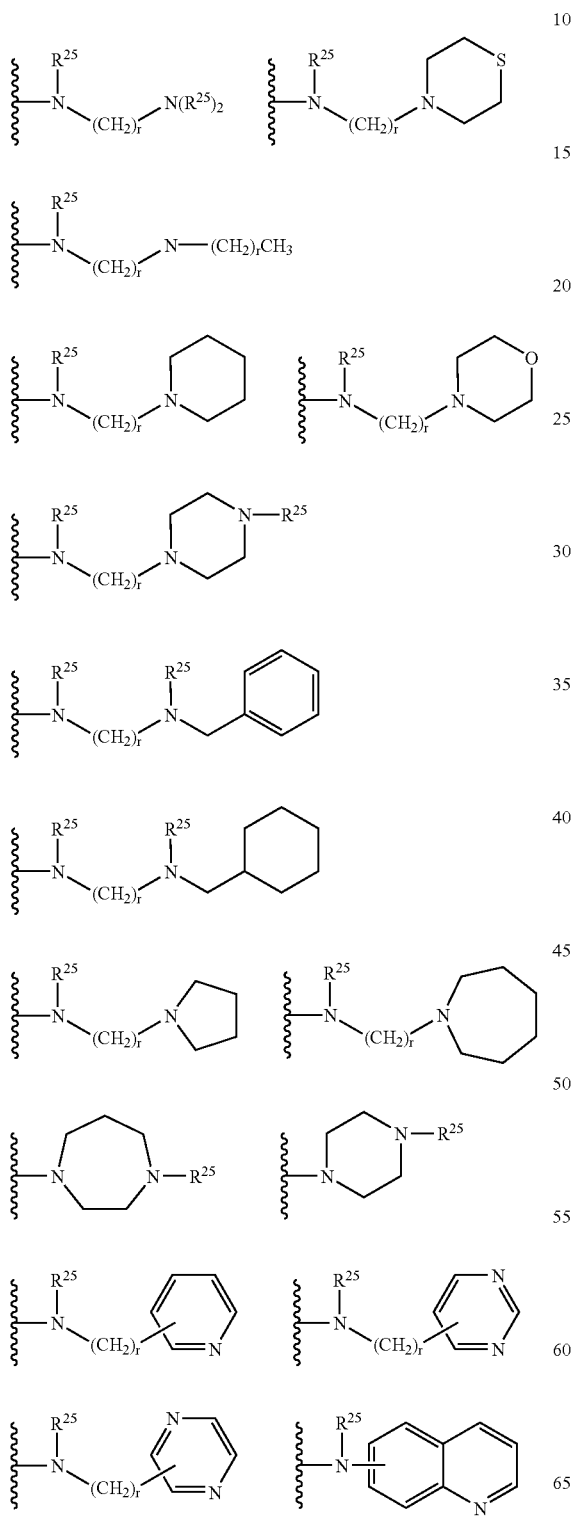

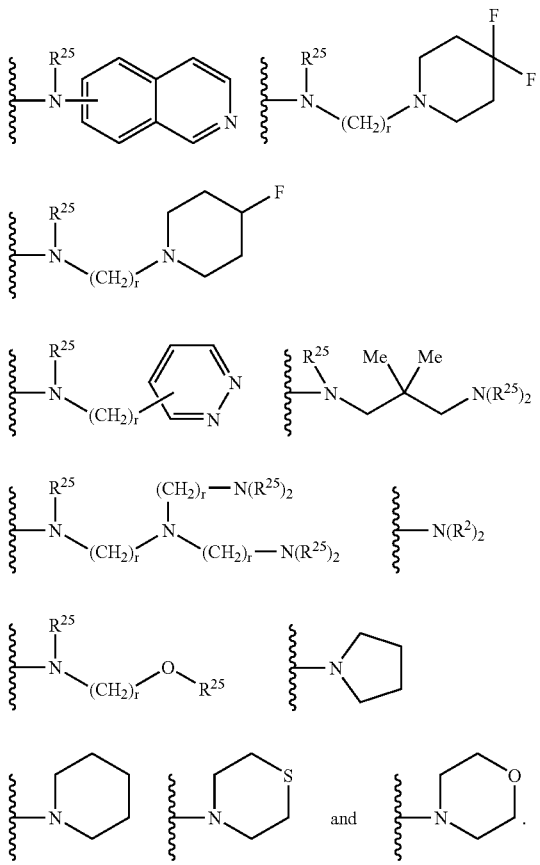

wherein r is an integer ranging from 2 to 8, inclusive (preferably 2 to 6), and each $R^{25}$ is independently H, $CH_3$, $CH_2CH_3$, $CH_2CH_2CH_3$, or $CH(CH_3)_2$. Preferred groups $N(R^{20})_2$ are selected from the group consisting of:

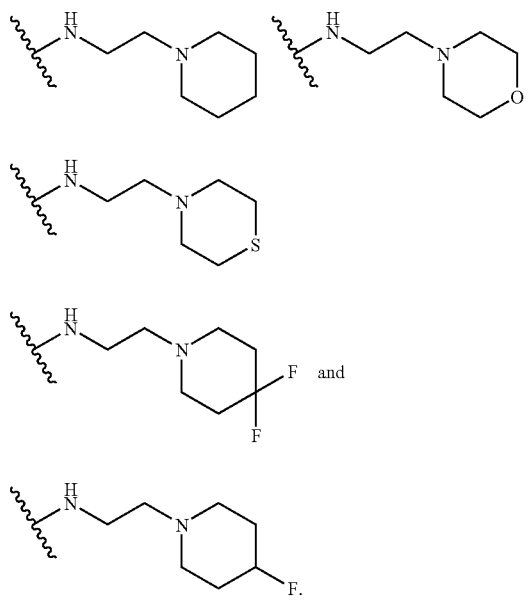

As used herein with reference to groups $R^1$, $R^2$, $R^3$, $R^{10}$, $R^{11}$, and $R^{20}$, the phrase "$C_1$ to $C_{16}$ alkyl group" includes not only conventional alkyl or cycloalkyl groups such as methyl, ethyl, propyl, isopropyl, butyl, s-butyl, isobutyl, t-butyl, cyclopentyl, cyclohexyl, and pentyl, but also unsaturated $C_1$ to $C_{16}$ groups, having for example aromatic, alkenyl, or alkynyl groups (e.g., phenyl, benzyl, vinyl, cyclohexenyl, etc.). One or more backbone carbons can be replaced by heteroatoms. There may be present functionalities such as hydroxy; oxo (=O); primary, secondary, or tertiary amine (e.g., —NH$_2$, —NH(CH$_3$), —N(CH$_3$)$_2$); quaternary ammonium (e.g., —N(CH$_3$)$_3^+$); alkoxy (e.g., methoxy, ethoxy); acyl (e.g., —C(=O)CH$_3$); amide (e.g., —NHC(=O)CH$_3$); thiol; thioether (e.g., —SCH$_3$); sulfoxide; sulfonamide (e.g., —SO$_2$NHCH$_3$); halogen (e.g., F, Cl); nitro; and the like. Exemplary specific $R^1$, $R^2$, $R^3$, $R^{10}$, $R^{11}$, and $R^{20}$ groups include methyl, trifluoromethyl, ethyl, acetyl, methoxy, methoxyethyl, ethoxyethyl, aminoethyl, hydroxyethyl, propyl, hydroxypropyl, cyclopropyl, isopropyl, 3-(dimethylamino)propyl, butyl, s-butyl, isobutyl, t-butyl, pentyl, cyclopentyl, vinyl, allyl, ethynyl, propynyl, and the like. Where a basic group is present (e.g., in a $R^{20}$ group) the $C_1$ to $C_{16}$ group preferably has a primary, secondary, or tertiary amine, amidine, or guanidine functionality.

Compounds of this invention have at least one basic group having a $pK_b$ of 12 or less. (Or, stated conversely, the conjugate acid of the basic group has a $pK_a$ greater than 2 ($pK_a=14-pK_b$).) Preferably, the $pK_b$ is less than 10, more preferably less than 5. A $pK_b$ of less than 12 ensures that, under the conditions in which the compound interacts with a nucleic acid, it is protonated. Preferably the basic group is a nitrogenous group, for example amine, amidine, guanidine, pyridine, pyridazine, pyrazine, pyrimidine, imidazole, or aniline. Primary, secondary, or tertiary aliphatic amines, are preferred.

Without being bound by theory, it is believed that the basic group enhances cell transport properties, enabling the compounds of this invention to be transported across cellular and nuclear membranes and to reach dsDNA in the nucleus. See Rothbard et al., WO 98/52614 (1998), which discloses that guanidine or amidino side chain moieties enhance transport across biological membranes. Another possible benefit is enhancement of the binding affinity to the nucleic acid, perhaps via ionic interactions with backbone phosphate groups. See Baird and Dervan, WO 98/37087 (1998) and Bruice et al., U.S. Pat. No. 5,698,674 (1997).

In a compound according to formula Ia, the basic group may be located on any of $R^1$, $R^2$, $R^3$, $R^{10}$, $R^{11}$, or $R^{20}$. Preferably, the basic group is locate on a $R^{20}$ group.

In a preferred embodiment of the invention, the thienyl compound has the formula Ib:

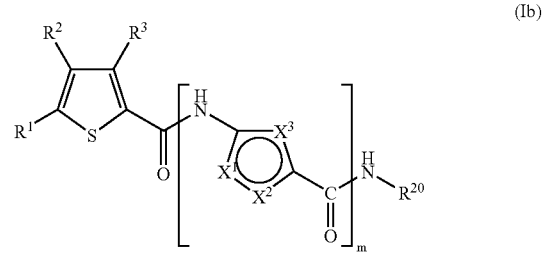

(Ib)

where m is 2, 3, 4, or 5 (preferably 3 or 4) and $R^1$, $R^2$, $R^3$, $R^{20}$, $X^1$, $X^2$, and $X^3$ are as and Xare as previously defined. When m is 2, at least one of $R^2$ and $R^3$ is F, Cl, Br, or I; when m is 3 or greater, at least one of $R^1$, $R^2$ and $R^3$ is F, Cl, Br, or I. Preferably, $R^1$ is not F, Cl, Br, or I when m is 2. Also preferably, $R^3$ is Cl. Preferred combinations of $R^1$, $R^2$ and/or $R^3$ include: (a) $R^1$ is H, $R^2$ is Br, and $R^3$ is Cl; (b) $R^1$ is H, $R^2$ is CH$_3$, and $R^3$ is Cl; and (c) $R^1$ and $R^2$ are each H and $R^3$ is Cl. Preferably, in formula Ib each

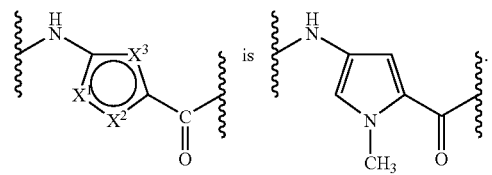

In another preferred embodiment of this invention, the thienyl compound has the formula Ic:

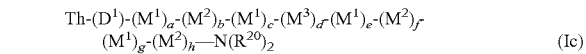

(Ic)

Th, $D^1$, $M^1$, $M^2$, $M^3$, and $R^{20}$ have the same meanings as previously assigned while subscripts a through h have these meanings: each of a, c, e, g and h is an integer independently ranging from 0 to 5, inclusive, while each of b, d, and f is independently 0 or 1. The sum of a, c, e, and g is at least 3.

In another preferred embodiment, compounds of this invention have the structure Id

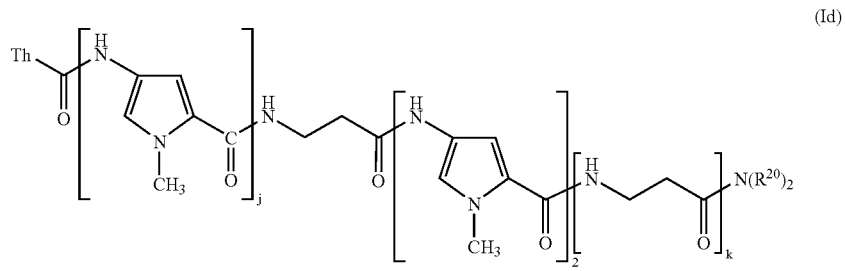

(Id)

where Th and $R^{20}$ are as previously defined, j is 1 or 2, and k is 0 or 1 (preferably 1). Exemplary compounds Id are shown in Table Id:

TABLE Id
| Compound. Ref. | Th—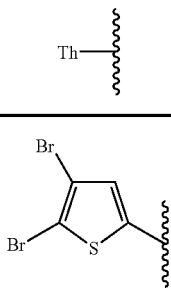 | j | k | 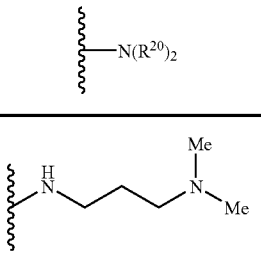—N(R[20])2 |
|---|---|---|---|---|
| Id-1 | 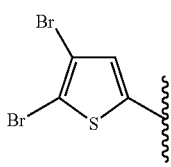 | 2 | 1 | 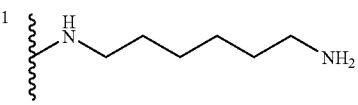 |
| Id-2 | 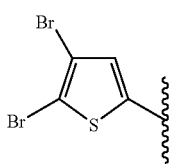 | 2 | 1 | 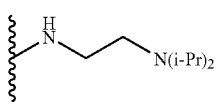 |
| Id-3 | 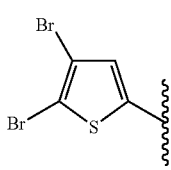 | 2 | 1 | 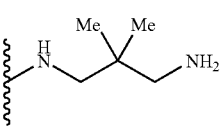 |
| Id-4 | 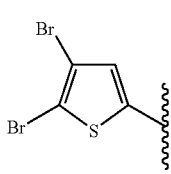 | 2 | 1 | 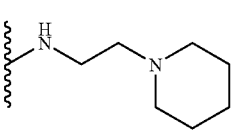 |
| Id-5 | 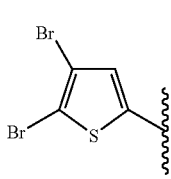 | 2 | 1 | 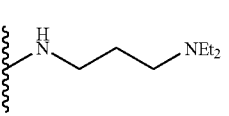 |
| Id-6 | 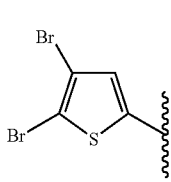 | 2 | 1 | 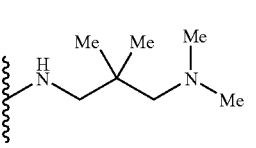 |
| Id-7 | | 2 | 1 | |

TABLE Id-continued

| Compound. Ref. | Th—⌇ | j | k | ⌇—N(R²⁰)₂ |
|---|---|---|---|---|
| Id-8 | 4,5-dibromothiophene | 2 | 1 | ⌇—NH—(CH₂)₄—NH₂ |
| Id-9 | 4,5-dibromothiophene | 2 | 1 | ⌇—NH—(CH₂)₃—NH₂ |
| Id-10 | 4,5-dibromothiophene | 2 | 1 | ⌇—N(Me)—CH₂CH₂—N(Me)₂ |
| Id-11 | 4,5-dibromothiophene | 2 | 1 | ⌇—NH—CH₂CH₂—morpholine |
| Id-12 | 4,5-dibromothiophene | 2 | 1 | ⌇—NH—CH₂CH₂—NH—Et |
| Id-13 | 4,5-dibromothiophene | 2 | 1 | ⌇—NH—(CH₂)₃—piperazine-NH |
| Id-14 | 4,5-dibromothiophene | 2 | 1 | ⌇—NH—(CH₂)₃—NEt₂ |
| Id-15 | 5-bromothiophene | 2 | 1 | ⌇—NH—(CH₂)₃—NH—cyclohexyl |
| Id-16 | 5-bromothiophene | 2 | 1 | ⌇—N(homopiperazine)—N—CH₃ |

TABLE Id-continued
| Compound. Ref. | Th—⟅ | j | k | —N(R[20])₂ |
|---|---|---|---|---|
| Id-17 |  | 2 | 1 | 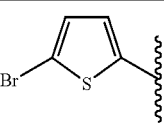 |
| Id-18 | 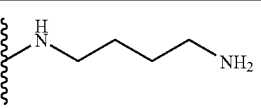 | 2 | 1 | 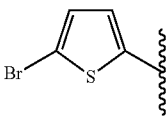 |
| Id-19 | 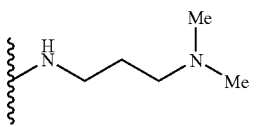 | 2 | 1 | 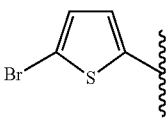 |
| Id-20 | 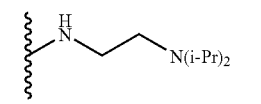 | 2 | 1 | 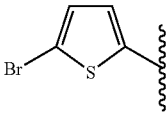 |
| Id-21 | 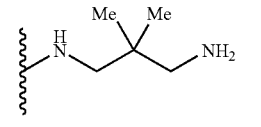 | 2 | 1 | 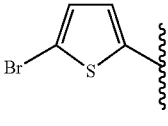 |
| Id-22 | 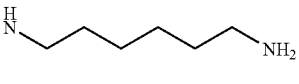 | 2 | 1 | 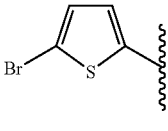 |
| Id-23 | 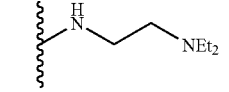 | 2 | 1 | 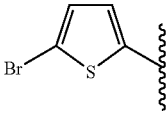 |
| Id-24 | 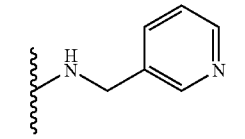 | 2 | 1 | 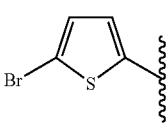 |
| Id-25 | 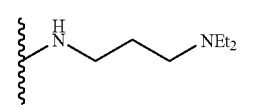 | 2 | 1 | 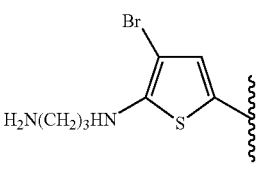 |
| Id-26 | 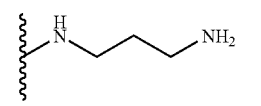 | 2 | 1 | 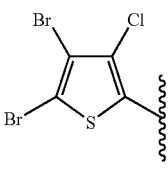 |

TABLE Id-continued

| Compound. Ref. | Th—✧ | j | k | ✧—N(R²⁰)₂ |
|---|---|---|---|---|
| Id-27 | 3-Cl-thiophen-2-yl | 2 | 1 | —NH—(CH₂)₃—N(Me)Me |
| Id-28 | 4-Cl-thiophen-2-yl | 1 | 1 | —NH—(CH₂)₃—N(Me)Me |
| Id-29 | 5-Cl-thiophen-2-yl | 1 | 1 | —NH—(CH₂)₃—N(Me)Me |
| Id-30 | 3-F-thiophen-2-yl | 2 | 1 | —NH—(CH₂)₃—N(Me)Me |
| Id-31 | 4-Br-3-OMe-thiophen-2-yl | 2 | 1 | —NH—(CH₂)₃—N(Me)Me |
| Id-32 | 4-Br-thiophen-2-yl | 2 | 0 | —NH—(CH₂)₄—NH₂ |

In another embodiment, thienyl compounds have the structure Ie:

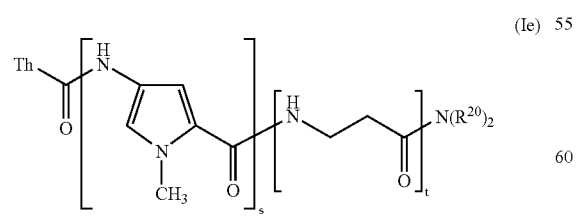

where Th and $R^{20}$ are as defined above, s is 3 or 4 (preferably 3), and t is 0 or 1. Illustrative compounds Ie are shown in Table Ie:

TABLE Ie
| Compound Ref. | Th- | s | t | -N(R20)2 |
|---|---|---|---|---|
| Ie-1 | 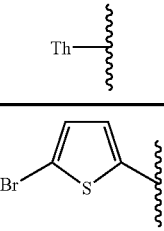 | 3 | 0 | 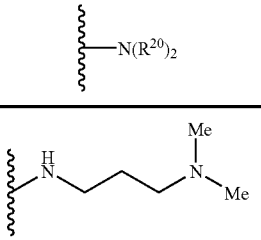 |
| Ie-2 | 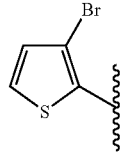 | 3 | 0 | 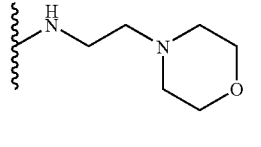 |
| Ie-3 | 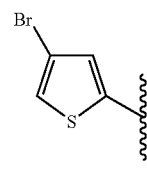 | 3 | 0 | 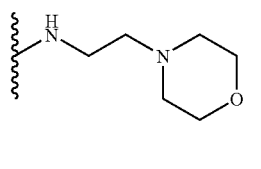 |
| Ie-4 | 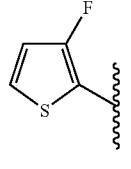 | 3 | 0 | 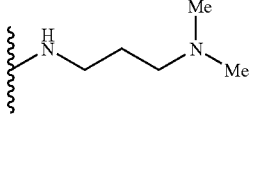 |
| Ie-5 | 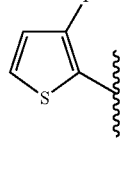 | 3 | 0 | 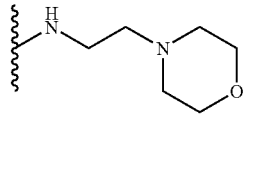 |
| Ie-6 | 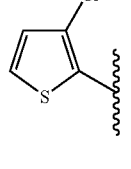 | 3 | 0 | 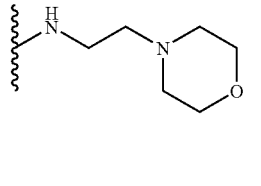 |
| Ie-7 | 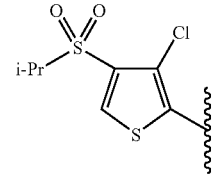 | 3 | 0 | 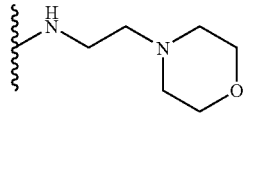 |

TABLE Ie-continued

| Compound Ref. | Th—⌇ | s | t | —N(R²⁰)₂ |
|---|---|---|---|---|
| Ie-8 | 3-chlorothien-2-yl | 3 | 0 | —NH-CH₂CH₂-N(Et)₂ |
| Ie-9 | 3-chlorothien-2-yl | 3 | 0 | —NH-CH₂CH₂-(thiomorpholin-4-yl) |
| Ie-10 | 3-chlorothien-2-yl | 3 | 0 | —NH-CH₂CH₂-(piperidin-1-yl) |
| Ie-11 | 3-chloro-4-methylthien-2-yl | 3 | 0 | —NH-CH₂CH₂-(morpholin-4-yl) |
| Ie-12 | 3-chlorothien-2-yl | 4 | 0 | —NH-CH₂CH₂-(morpholin-4-yl) |
| Ie-13 | 3-chlorothien-2-yl | 3 | 0 | —NH-CH₂CH₂-(4-fluoropiperidin-1-yl) |
| Ie-14 | 4-bromo-3-chlorothien-2-yl | 3 | 0 | —NH-CH₂CH₂-(thiomorpholin-4-yl) |
| Ie-15 | 4-bromo-3-chlorothien-2-yl | 3 | 0 | —NH-CH₂CH₂-(piperidin-1-yl) |

In yet another embodiment compounds have formula If:

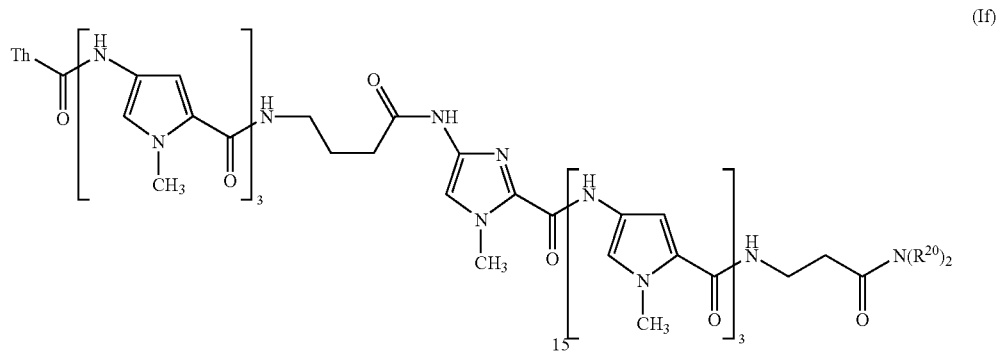

Compounds If are characterized by a "hairpin" provided by γ-aminobutyric acid residue. Illustrative compounds If are shown in Table If.

TABLE If

| Compound Ref. | Th— | —N(R$^{20}$)$_2$ |
|---|---|---|
| If-1 | 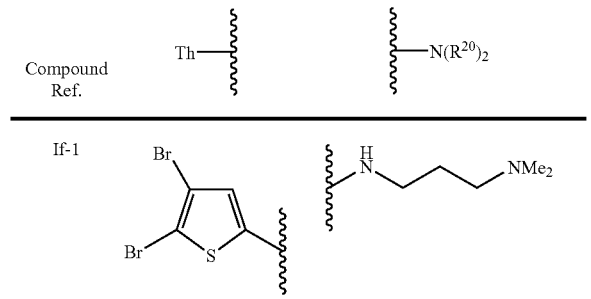 | |
| If-2 | 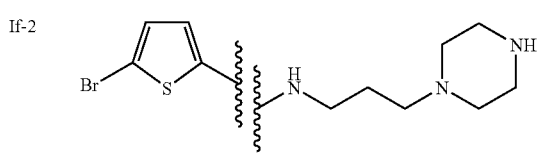 | |

TABLE If-continued

| Compound Ref. | Th— | —N(R$^{20}$)$_2$ |
|---|---|---|
| If-3 | 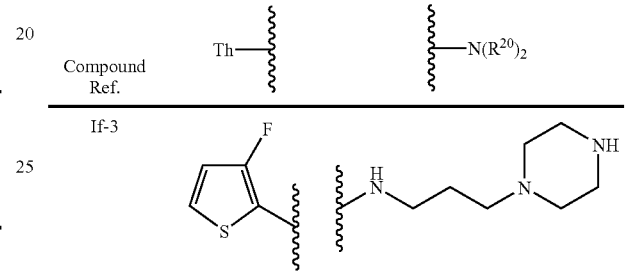 | |

In yet another embodiment, compounds of this invention have the structure Ig

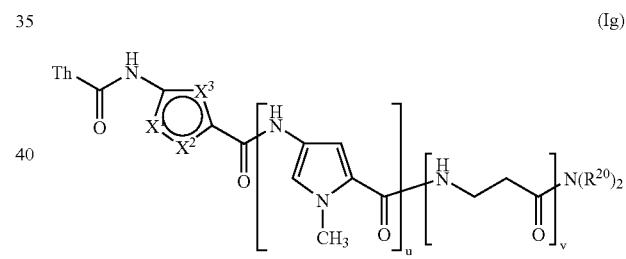

where Th, X$^1$, X$^2$, X$^3$, and R$^{20}$ are as defined above; u is 1 or 2, and v is 0 or 1. Exemplary compounds Ig are shown in Table Ig:

TABLE Ig

| Compound Ref. | Th— | (X group) u | v | —N(R$^{20}$)$_2$ |
|---|---|---|---|---|
| Ig-1 | | | 2 | 0 | 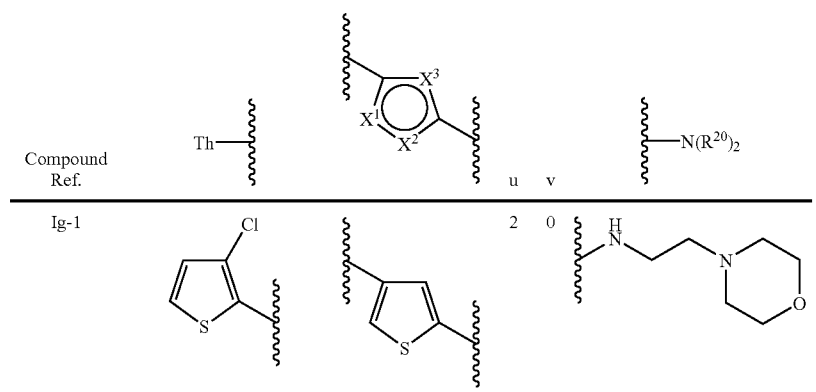 |

TABLE Ig-continued

| Compound Ref. | Th— | X¹—X³ / X² (u, v) | u | v | —N(R²⁰)₂ |
|---|---|---|---|---|---|
| Ig-2 | 3-chlorothien-2-yl | 1-(CH₂)₃OH-pyrrole-2,4-diyl | 2 | 1 | NH-CH₂CH₂-morpholine |
| Ig-3 | 3-chlorothien-2-yl | 1-(CH₂)₃OSO₃⁻-pyrrole-2,4-diyl | 2 | 1 | NH-CH₂CH₂-morpholine |
| Ig-4 | 3-chloro-4-(i-Pr-SO₂)-thien-2-yl | thiophene-2,4-diyl | 2 | 0 | NH-CH₂CH₂-morpholine |
| Ig-5 | 3-fluorothien-2-yl | thiophene-2,4-diyl | 2 | 0 | NH-CH₂CH₂-morpholine |
| Ig-6 | 4-bromo-3-methoxy-thien-2-yl | 1-Me-imidazole-2,4-diyl | 2 | 0 | NH-CH₂CH₂-morpholine |
| Ig-7 | 4,5-dibromo-3-hydroxy-thien-2-yl | 1-Me-imidazole-2,4-diyl | 2 | 0 | NH-CH₂CH₂-morpholine |
| Ig-8 | 3-chlorothien-2-yl | 1-Me-imidazole-2,4-diyl | 2 | 0 | NH-CH₂CH₂-morpholine |

TABLE Ig-continued
| Compound Ref. | Th— | X¹–X²–X³ ring u v | —N(R²⁰)₂ |
|---|---|---|---|
| Ig-9 | Me, Cl thiophene | imidazole N-Me, 2 0 | NH-CH₂CH₂-morpholine |
| Ig-10 | Br, Cl thiophene | imidazole N-Me, 2 0 | NH-CH₂CH₂-thiomorpholine |
Those skilled in the art will appreciate that the invention encompasses many other structural motifs, for instance
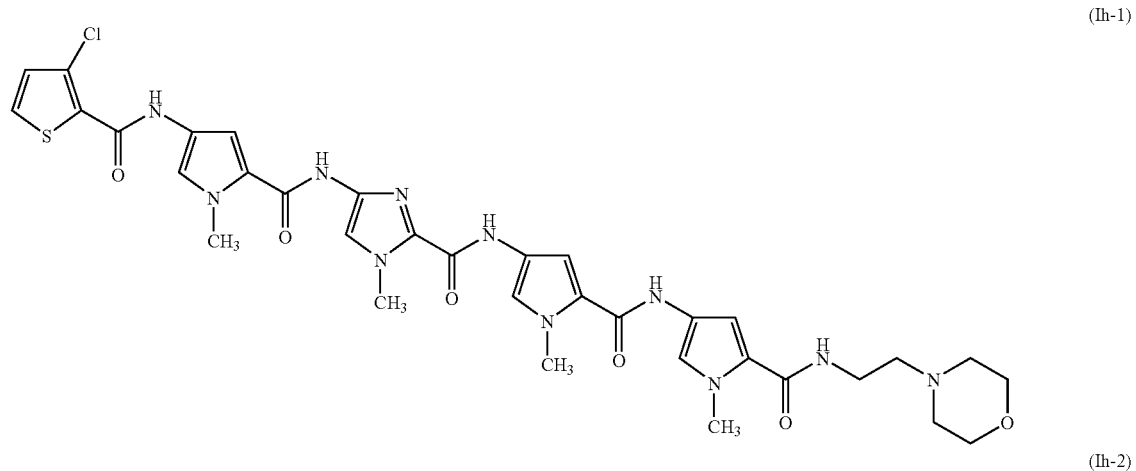
(Ih-1)
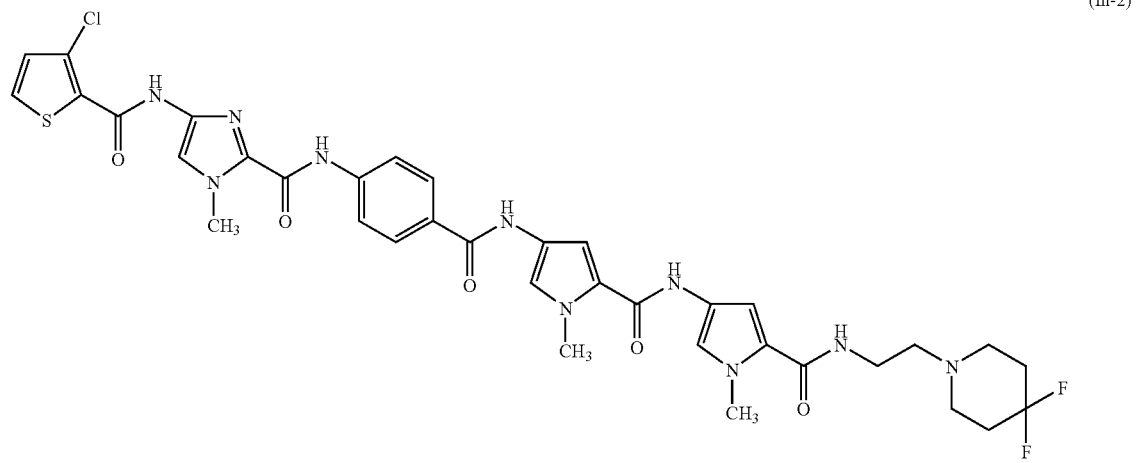
(Ih-2)

A thienyl compound of this invention can be tethered or linked to another nucleic acid binding compound, such combinations being referred to as tandem-linked nucleic acid binding compounds. The tandem-linked compounds can be two identical thienyl compounds according to this invention, two different thienyl compounds according to this invention, or one thienyl compound according to this invention and a different, non-thienyl nucleic acid binder. A preferred site for forming the tandem link is an amino, hydroxy, or thiol functionality in a group L in moiety $M^2$, which can be acylated or alklylated. The preparation of tandem linked nucleic acid binding polyamides in this manner is disclosed in Baird et al., WO 98/45284 (1998), the disclosure of which is incorporated herein by reference. Other potential sites for the formation of tandem links are at Th (via substituents $R^1$, $R^2$, and $R^3$), at moieties $M^1$ (substituents $R^{10}$ and $R^{11}$) and at the group $R^{20}$.

Compounds of this invention can be conjugated to other moieties, such as oligonucleotides, peptides, proteins, fluorophores or other reporter groups, and the like.

Compounds of this invention preferably bind to dsDNA with high affinity, meaning an equilibrium association constant of at least $10^3$ $M^{-1}$, more preferably at least $10^6$ $M^{-1}$, and most preferably at least $10^9$ $M^{-1}$. The measurement of binding affinities by quantitative DNase I footprinting is disclosed in Dervan, WO 98/50582 (1998), and Trauger et al., Nature 382, 559 (8 Aug. 1996); the disclosures of which are incorporated herein by reference.

Because they are strong binders, compounds of this invention can be used to form complexes with dsDNA, for the purpose of recognizing and/or isolating dsDNA strands containing particular base-pair sequences, for example for analytical or diagnostic purposes. Thus, in another aspect of this invention there is provided a complex between dsDNA and compound of this invention. In cellular systems or in living organisms, they can modulate the expression of a gene by binding to the gene or a promoter or repressor region thereof. Such modulation may be useful for therapeutic or research purposes.

Additionally, compounds of this invention have been found to have anti-bacterial properties and therefore may be used for combating (i.e., preventing and/or treating) infections in eukaryotic organisms. Other pathogens against which compounds of this invention can be useful include protozoa and viruses. For human anti-infective applications, an effective amount of a compound of this invention is used, optionally in combination with a pharmaceutically acceptable carrier. The composition may be dry, or it may be a solution. Treatment may be reactive, for combating an existing infection, or prophylactic, for preventing infection in an organism susceptible to infection. Preferably, compounds of this invention are used to treat infections by drug-resistant strains of bacteria. By "drug-resistant" it is meant that the bacteria are resistant to treatment with conventional, non-polyamide antibiotics. Thus, compounds of this invention can be used for the preparation of medicaments for treating infections by pathogens, especially Gram-positive bacteria.

Host organisms that can be treated include eukaryotic organisms, in particular plants and animals. The plant may be an agriculturally important crop, such as wheat, rice, corn, soybean, sorghum, and alfalfa. Animals of interest include mammals such as bovines, canines, equines, felines, ovines, porcines, and primates (including humans).

While not wishing to be bound by any particular theory, it is believed that the compounds of this invention derive their biological activity from their ability to bind to dsDNA, in combination with other characteristics associated with the halogenated thienyl group. As deducible from the biological activity and DNA binding results presented hereinbelow, DNA binding capability alone appears to be an insufficient parameter for the manifestation of biological activity.

A specific target pathogen may be screened against a library of compounds to determine which one(s) are effective against it. Conversely, a specific compound may be screened against a number of pathogens, to determine which one(s) it is effective against.

The practice of this invention can be further understood by reference to the following examples, which are provided by means of illustration and not of limitation.

Starting Materials, Intermediates, and Reagents; Instrumentation

General

Methyl 4-amino-1-methyl-pyrrole-2-carboxylate ("H-Py-OMe") hydrochloride, 4-[(t-butoxycarbonyl)amino]-1-methylpyrrole-2-carboxylic acid ("Boc-Py-OH"), 4-[(t-butoxycarbonyl)amino]-1-methyl-imidazole-2-carboxylic acid ("Boc-Im-OH"), and (γ-[(t-Butoxycarbonyl)amino]-butyric acid-(4-carboximido-1-methyl-imidazole)-2-carboxylic acid ("Boc-γ-Im-OH") were prepared as described in Baird and Dervan, J. Am. Chem. Soc., 1996, 118, 6141.

Boc-β-alanine-(4-carboxamidomethyl)-benzyl-ester-copoly (styrene-divinylbenzene) resin ("Boc-β-alanine-PAM Resin," 0.86 mmol/g substitution), 2-(1H-benzotriazole-1-yl)-1,1,3,3-tetramethyluronium hexafluorophosphate ("HBTU"), Boc-γ-aminobutyric acid, and Boc-β-alanine-OH were purchased from Peptides International, Louisville, Ky. 3-Chlorothiophene-2-carboxylic acid and 2,3-dibromothiophene-5-carboxylic acid were purchased from Lancaster Synthesis. 5-Bromothiophene-2-carboxylic acid was from Avocado Organics. 1-(2-Aminoethyl)piperidine, N,N,2,2-tetramethyl-1,3-propanediamine, 3-(dimethylamino) propylamine ("H-Dp"), 4-(2-aminoethyl)morpholine, N,N,N-trimethylethylenediamine, 1-(2-aminoethyl)piperazine, N-cyclohexyl-1,3-propanediamine, 1-methylhomopiperazine, N-methylpyrrole and N-methylimidazole were from Sigma-Aldrich, Inc. 1,6-diaminohexane, 2,2-dimethyl-1,3-propanediamine, 3-diethylaminopropylamine, N,N-diethylaminediamine and 3-(aminomethyl)pyridine were purchased from TCI AMERICA. 2-Ethylaminoethylamine and N,N-diisopropylethylenediamine were purchased from Fluka. 1,3-Diaminopropane and 1,4-diaminobutane were purchased from Acros Organics.

All reagents and solvents were used without further purification, except where noted otherwise.

HPLC chromatography was done on either a Varian or a Gilson HPLC with a PRP-1, 2.5 inch $C_{18}$ column (particle size 12–20 μm, 250 mm×101.6 mm), from Hamilton. $^1$H NMR spectra were taken on a Varian 400 NMR, operating at 400 MHz.

Synthesis of Boc-Py-Py-OH

The synthesis of Boc-Py-Py-OH is summarized in Scheme 1.

Scheme 1

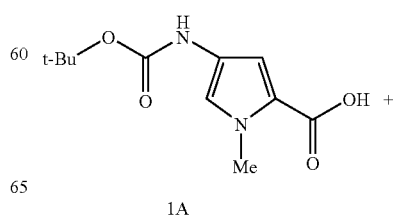

1A

-continued

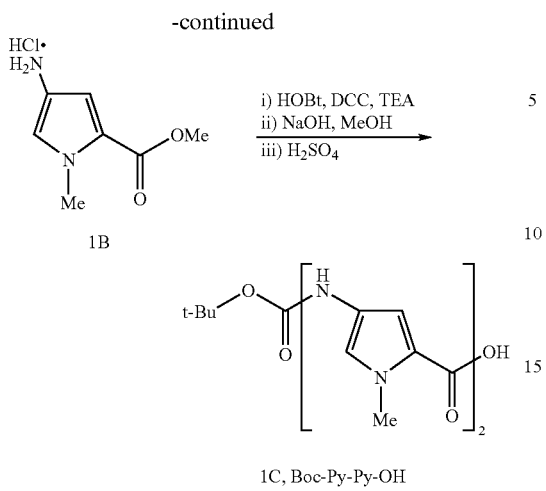

1B i) HOBt, DCC, TEA
ii) NaOH, MeOH
iii) H$_2$SO$_4$

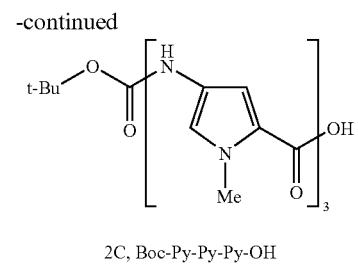

1C, Boc-Py-Py-OH

To a solution of Boc-Py-OH (1A, 40 g, 167 mmol) in 150 mL DMF was added 1.2 eq hydroxybenzotriazole ("HOBt," 27 g, 0.2 mmol) followed by 1.2 eq dicyclohexylcarbodiimide ("DCC," 40.4 g, 0.2 mmol). The solution was stirred for 5 hours at room temperature, after which the DCC was removed by filtration followed by a rinse with N,N-dimethylformamide ("DMF," 50 mL). H-Py-OMe hydrochloride (1B, 34 g, 160 mmol) was added, followed by triethylamine ("TEA," 80 mL) and the reaction was stirred at 50° C. for 10 hr. The reaction mixture was then added dropwise to a stirred solution of ice water (2 L) and the solution placed at 4° C. overnight. The resulting precipitate was collected by vacuum filtration and dried overnight to provide methyl 4-[t-butoxycarbonyl)amino]-1-methylpyrrole-2-(4-carboxamido)-1-methylpyrrole-2-carboxylate (53 g, 83% yield). The ester was dissolved in methanol (200 mL), NaOH (3M, 200 mL) was added, and the resulting mixture stirred for 3 hours at 50° C. Excess methanol was removed in vacuo and the resulting solution acidified to pH 3 using H$_2$SO$_4$. The resulting precipitate was collected by filtration and dried in vacuo to yield Boc-Py-Py-OH (1C) as a white powder (43 g, 90% yield).

Synthesis of Boc-Py-Py-Py-OH

Boc-Py-Py-Py-OH was synthesized by the route shown in Scheme 2:

Scheme 2

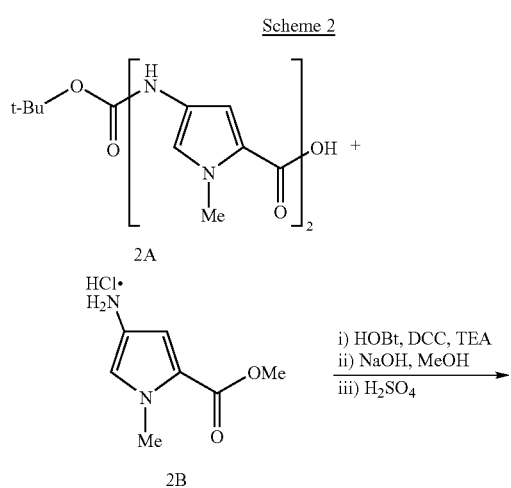

2A

2B i) HOBt, DCC, TEA
ii) NaOH, MeOH
iii) H$_2$SO$_4$

-continued

2C, Boc-Py-Py-Py-OH

To a solution of Boc-Py-Py-OH (2A, 60.4 g, 167 mmol) in 150 mL DMF was added 1.2 eq HOBt (27 g, 0.2 mmol) followed by 1.2 eq DCC (40.4 g, 0.2 mmol). The solution was stirred for 5 hours at room temperature, after which the DCC was removed by filtration followed by a rinse with DMF (50 mL). H-Py-OMe hydrochloride (2B, 34 g, 160 mmol) was added, followed by TEA (80 mL) and the reaction was stirred at 50° C. for 10 hours. The reaction mixture was then added dropwise to a stirred solution of ice water (2 L) and the solution stored at 4° C. overnight. The resulting precipitate was collected by vacuum filtration and dried overnight to provide methyl 4-[t-butoxycarbonyl)amino]-1-methylpyrrole-2-[4-carboxamido-1-methylpyrrole-2-(4-carboxamido-1-methylpyrrole)]-2-carboxylate.

The ester was dissolved in methanol (200 mL), NaOH (3M, 200 mL) was added, and the resulting mixture stirred for 3 hours at 50° C. Excess methanol was removed in vacuo and the resulting solution acidified to pH 3 using H$_2$SO$_4$. The resulting precipitate was collected by filtration and dried in vacuo to yield Boc-Py-Py-Py-OH (2C) as a white powder.

Synthesis of 3-fluorothiophene-2-carboxylic acid

This example describes the synthesis of 3-fluorothiophene-2-carboxylic acid via the diazonium salt, by the route described in Scheme 3:

Scheme 3

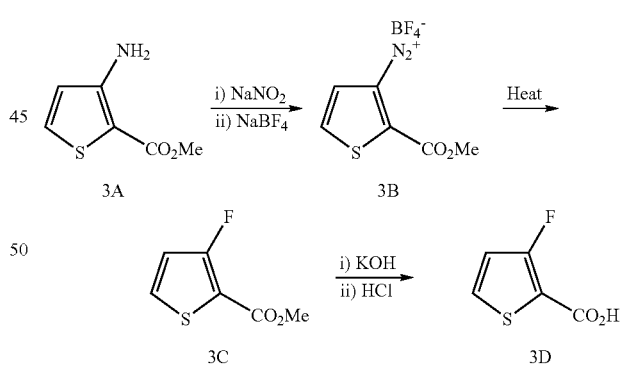

Formation of the diazonium salt 3B. A suspension of aminothiophene ester 3A (2 g, 12.72 mmol) in conc. aq. HCl (10 mL) and H$_2$O (20 mL) was treated dropwise with a solution of NaNO$_2$ (1.1 gram, 15.74 mmol) in H$_2$O (5 mL) at 0° C. The mixture was stirred at 0° C. for 20 minutes and treated with NaBF$_4$ (10 g) in H$_2$O (saturated). The solids were collected by filtration and washed with ice water, treated with tetrahydrofuran ("THF"), dried (MgSO$_4$), and evaporated.

Formation of the fluoride 3C. The crude diazonium salt 3B was distributed in a glass tube under a strong flow of N$_2$ that was passed through a cooling trap. The material was heated until the vigorous evolution of a gas that condensed upon cooling. The condensed material was collected with ethyl acetate ("AcOEt"). Evaporation gave fluorothiophene ester 3C (720 mg) as a brown liquid.

Saponification of the ester 3C. A solution of the ester 3C (700 mg) and KOH (5 mL, 2 M) in ethanol (5 mL) was stirred for 28 hr at room temperature and diluted with $H_2O$ (25 mL). The mixture was washed with AcOEt (2x) and acidified to pH 2 with 1M aq. HCl. Extraction of the mixture with AcOEt (2x), drying (MgSO$_4$) of the combined organic layers and evaporation gave 3-fluorothiophene-2-carboxylic acid 3D (667 mg) as a brown solid.

Synthesis of H-Py-Py-Py-Dp and H-Py-Py-Dp

Scheme 4 summarizes the synthesis of H-Py-Py-Py-Dp and its isolation as the trifluoroacetate salt.

Scheme 4

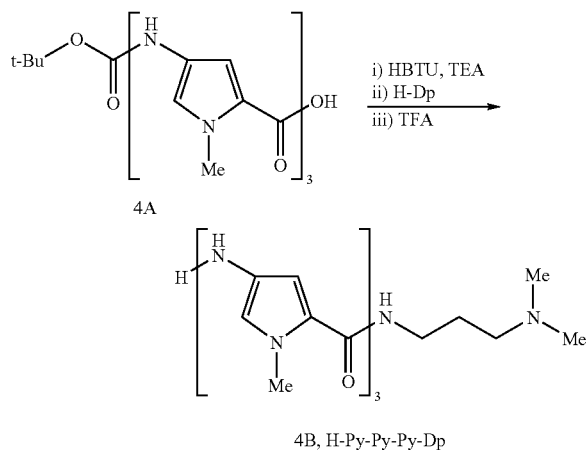

4B, H-Py-Py-Py-Dp

Boc-Py-Py-Py-OH (4A, 4.68 g, 0.1 mmol, 1 eq) was activated with HBTU (3.4 g, 0.095 mmole, 0.95 eq) in 50 mL DMF and 25 mL TEA for 45 minutes at room temperature. H-Dp (12 mL, 0.12 mmol, 1.2 eq) was added to the mixture and the reaction was stirred at 37° C. overnight. The product mixture was concentrated in vacuo and trifluoroacetic acid ("TFA," 150 mL) was added to the reaction, which was then stirred at room temperature for 3 hours. The solution was concentrated in vacuo, after which acetic acid (40 mL) and water (200 mL) was added. The solution was extracted with diethyl ether three times, then product 4B was purified using reverse phase HPLC with a gradient of 1% acetonitrile/minute in 0.5% acetic acid.

Using an analogous procedure, the trifluoroacetate salt of H-Py-Py-Dp was prepared.

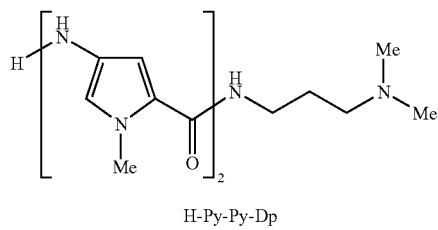

H-Py-Py-Dp

Synthesis of H-Py-Py-Py-2-aminoethylmorpholine

Scheme 5 summarizes the synthesis of H-Py-Py-Py-4-(2-aminoethylmorpholine) (5B) and its isolation as the trifluoroactetate salt.

Scheme 5

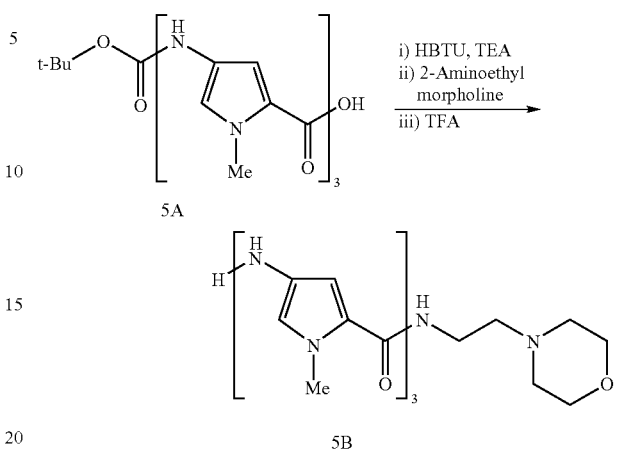

Boc-Py-Py-Py-OH (5A, 4.68 g, 0.1 mmol, 1 eq) was converted to compound 5B using the procedure describe above for H-Py-Py-Py-Dp, using 4-(2-aminoethylmorpholine) (3 mL, 0.12 mmol, 1.2 eq) instead of H-Dp.

Synthesis of 1-(methoxymethyl)-4-(Boc-amino)pyrrole-2-carboxylic acid

The synthesis of 1-(methoxymethyl)-4-(Boc-amino)pyrrole-2-carboxylic acid (5D), used in the synthesis of compound Ig-10, is summarized in Scheme 5A:

Scheme 5A

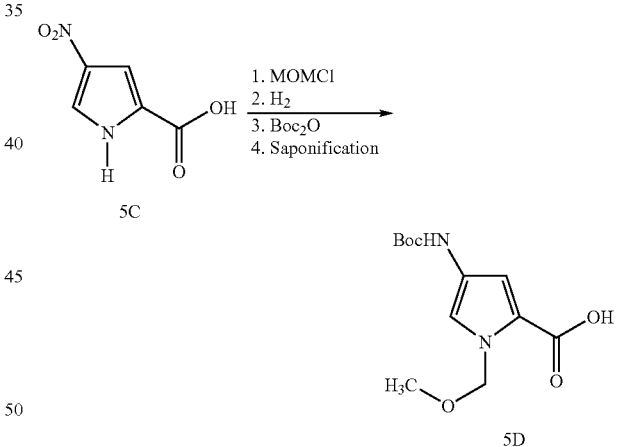

Ethyl 4-nitropyrrole-2-carboxylate (5C) was alkylated with methoxymethyl chloride (MOMCl), followed by hydrogenation (Pd catalyst) and protection with Boc anhydride (Boc$_2$O). Saponification gave acid 5C.

Synthesis of Compounds

Solution Phase Synthesis—General

Compounds of this invention can be made by solution phase methods. Generally, the method begins with one of two short polyamide precursors, e.g., Boc-Py-Py-Py-OH or Boc-Py-Py-OH, and consists of 4 steps: the addition of an amine to the C-terminus of the polyamide precursor, the deprotection of the polyamide by the removal of the t-butoxycarbonyl (Boc) group from the N-terminus, activation with HBTU of the desired carboxylic acid group, and the coupling of the activated amino acid or amino acid chain to the polyamide. After activating the polyamide using a molar equivalent of HBTU in a solution of TEA and DMF for 45 min, the amine was added and coupling was allowed to proceed overnight. The protecting Boc group was removed by adding 100% TFA to the reaction mixture and mixing for 3 hours. The solvent was removed and the resulting solid was dissolved in acetic acid/water and impurities were extracted. The intermediate polyamide was purified using reversed phase preparative HPLC with a gradient of 1% acetonitrile/minute in 0.5% acetic acid. The amino acids to be coupled to the intermediate polyamide were activated using a molar equivalent of HBTU in N-methylpyrrolidone ("NMP") and TEA (2:1) for 20 minutes. The activated amino acid was then added to the deprotected polyamide and the mixture was heated to 37° C. and mixed or shaken for 2 hours. The final polyamide was then purified using reversed phase preparative HPLC with a gradient of 1% acetonitrile/minute in 0.5% acetic acid.

Synthesis of Compounds Ie-1

The solution phase synthesis of compounds of general structure Ie is illustrated with specific reference to compound Ie-1, identified in Scheme 6 as compound 6C:

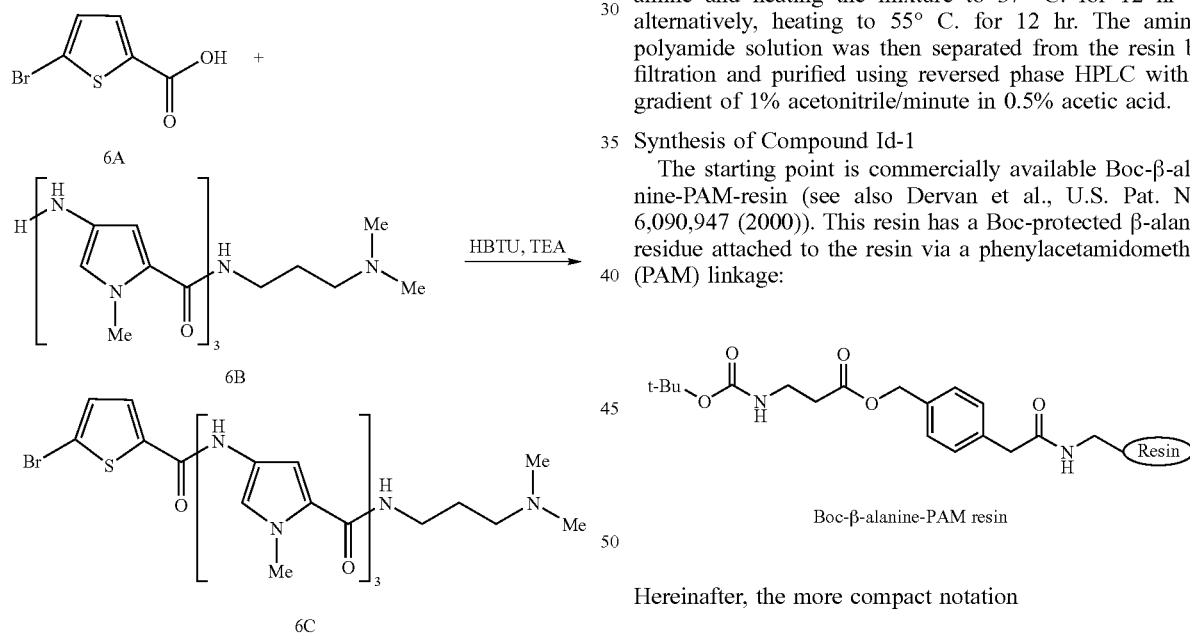

5-Bromothiophene-2-carboxylic acid (6A, 2 g., 10 mmol, 1.2 eq.) was activated with HBTU (3.7 g., 9.8 mmol, 1.14 eq.) in DMF (20 mL) and TEA (13 mL). The solution was stirred for 10 minutes at room temperature, after which H-Py-Py-Py-DP (6B, 4 g., 8.5 mmol, 1 eq., as the trifluoroacetate salt synthesized as described above) was added as a solid. DMF (4 mL) was added to complete the transfer of the solid material, and the resulting solution was stirred at 37° C. overnight. The reaction was then dried in vacuo, 10% aqueous acetic acid (200 mL) was added and the product was purified using reversed phase preparative HPLC to yield compound Ie-1.

Other compounds Ie such as Ie-2, Ie-3, Ie-4, Ie-5, and Ie-6 were prepared by substituting the building blocks corresponding to the appropriate Th- and $N(R^{20})_2$ groups in the steps above.

Solid Phase Synthesis—General

Compounds of this invention can be synthesized by the solid phase method of Baird and Dervan, *J. Am. Chem. Soc.*, 1996, 118, 6141, using Boc-β-alanine-PAM-Resin, 0.86 mmol/g substitution. The method consists of 3 step cycles—deprotection of the resin by the removal of the t-butoxycarbonyl (Boc) group from the N-terminus, activation with HBTU of the amino acid or amino acid oligomer to be coupled to the deprotected resin, and the coupling of the activated amino acid or amino acid chain to the deprotected resin, followed by a single step that cleaves the polyamide from the resin.

Generally, the protecting Boc group was removed by swelling the resin with a $CH_2Cl_2$ wash, then adding 100% TFA to the resin and mixing for 20 minutes, after which the TFA was removed with a wash of $CH_2Cl_2$, methanol and NMP. Amino acids were activated using a molar equivalent of HBTU in a solution of NMP and TEA (1:1) for 20 minutes, and then NMP was added to bring the solution to a 2:1 NMP/TEA ratio. The activated amino acid was then added to the deprotected resin and the mixture was heated to 37° C. and mixed or shaken for 2 hours. After the desired amino acids had been added to the resin, the polyamide was cleaved from the Boc-β-alanine-PAM resin by adding neat amine and heating the mixture to 37° C. for 12 hr or alternatively, heating to 55° C. for 12 hr. The amine/polyamide solution was then separated from the resin by filtration and purified using reversed phase HPLC with a gradient of 1% acetonitrile/minute in 0.5% acetic acid.

Synthesis of Compound Id-1

The starting point is commercially available Boc-β-alanine-PAM-resin (see also Dervan et al., U.S. Pat. No. 6,090,947 (2000)). This resin has a Boc-protected β-alanyl residue attached to the resin via a phenylacetamidomethyl (PAM) linkage:

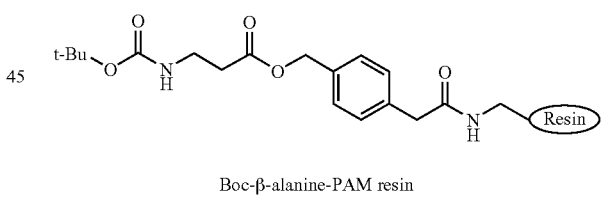

Boc-β-alanine-PAM resin

Hereinafter, the more compact notation

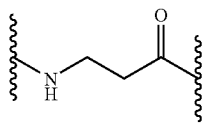

will be used for convenience, where "β" represents and "PAM" represents

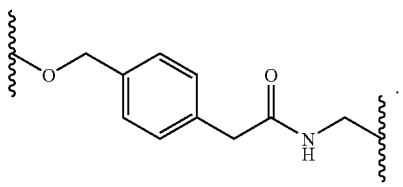

The solid phase procedure is described following with specific reference to compound Id-1, as illustrative for compounds of Table Id. The synthetic scheme is summarized in Scheme 7, with compound Id-1 identified there as 7F:

resin was washed using wash cycle B. Boc-Py-Py-OH (125 mg, 0.34 mmol) was then activated with HBTU (121 mg, 0.34 mmol) in NMP (0.66 mL) and TEA (0.33 mL) and added to the deprotected resin in a 2:1 solution NMP/TEA (1.0 mL). The Quest automated coupling step was used, followed by wash cycle A, to yield Boc-Py-Py-β-PAM resin (7B). In the second cycle, Boc-β-alanine-OH (65 mg, 0.34 mmol) was used instead of the Boc-Py-Py-OH, all other steps remaining the same, to form H-β-Py-Py-β-PAM resin (7C). In the third cycle, the first cycle was repeated to form Boc-Py-Py-β-Py-Py-β-PAM resin (7D).

In the last cycle, the addition of 2,3-dibromothiophene-5-carboxylic acid to Boc-Py-Py-β-Py-Py-β-PAM resin, compound 7D was deprotected and washed using wash cycle B. 2,3-Dibromothiophene-5-carboxylic acid (98.4 mg, 0.34 mmol) was then activated and added to the deprotected Scheme 7

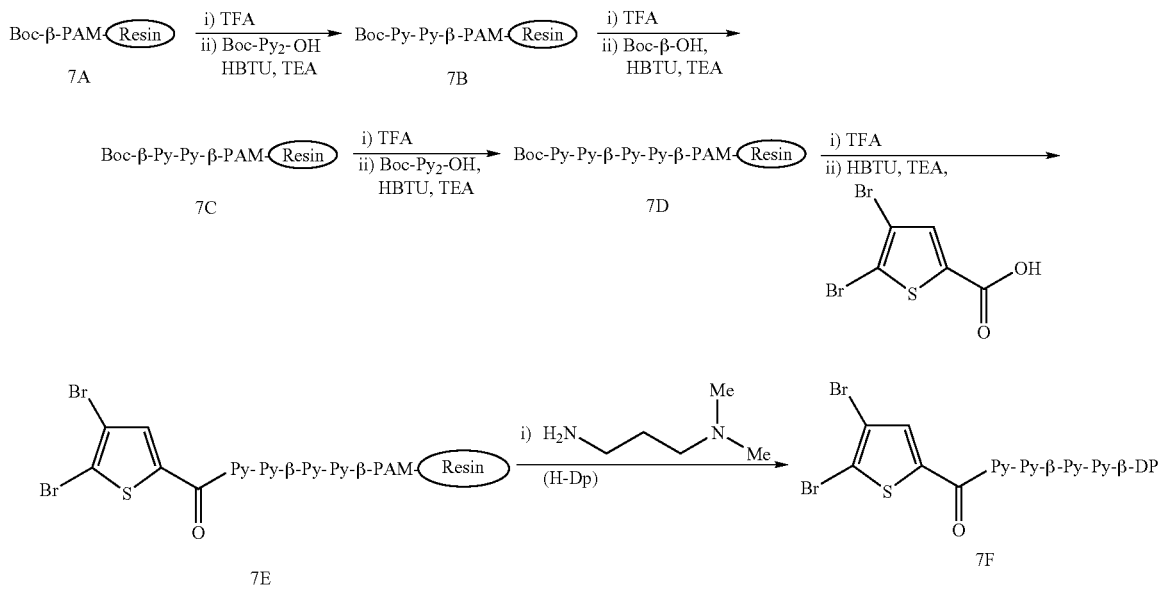

Compound Id-1 was synthesized on an Argonaut Quest 210 semi-automated synthesizer. This instrument has 20 disposable reaction vessels with volumes 10 of mL each, which can be washed, heated, mixed and drained using automated cycles or manually. Wash cycle A consists of three steps—step one is three cycles of adding NMP (5 mL) to each vessel, mixing for 2 minutes and draining the NMP from the vessels using a controlled flow of compressed nitrogen, steps two and three are the same as step one, but with the substitution of methanol and $CH_2Cl_2$, respectively, for NMP. Wash cycle B uses the same three steps as wash cycle one, using $CH_2Cl_2$, methanol and NMP in that order. The coupling cycle consists of heating the vessels to 37° C. and mixing for 2 hours. In the cleavage cycle, the vessels are heated to either 55° C. or 90° C. and mixed for 12 hours.

In the first cycle for the synthesis of compound Id-1, Boc-β-alanine-PAM resin (7A, 200 mg) was placed in a vessel and manually washed with $CH_2Cl_2$. The protecting Boc group was then removed by manually adding 100% TFA (5 mL) and mixing for 20 minutes. The deprotected resin in a solution NMP/TEA (2:1, 1.0 mL). The automated coupling step was used, followed by wash cycle A and a manual wash with NMP to yield 2,3-dibromothiophene-5-Py-Py-β-Py-Py-β-PAM resin (7E). The polyamide was cleaved from the resin by adding dimethylaminopropylamine (H-Dp, 3 mL) and using the automated cleavage cycle at 55° C. then purified by reversed phase preparative HPLC to yield compound Id-1 (7F), characterized by NMR.

Other compounds of formula Id, such as Id-2, Id-3, Id-4, Id-5, Id-6, Id-7, Id-8, Id-9, Id-10, Id-11, Id-12, Id-13, Id-15, Id-16, Id-17, Id-18, Id-19, Id-20, Id-21, Id-22, Id-23, Id-24, Id-25, Id-26, Id-27 and Id-30 were made by substituting the building blocks corresponding to the appropriate Th- and $N(R^{20})_2$ groups in the steps above.

Synthesis of Compound If-2

The solid phase synthesis of compounds If is now illustrated, with specific reference to compound If-2, identified as compound 8F in scheme 8:

Scheme 8

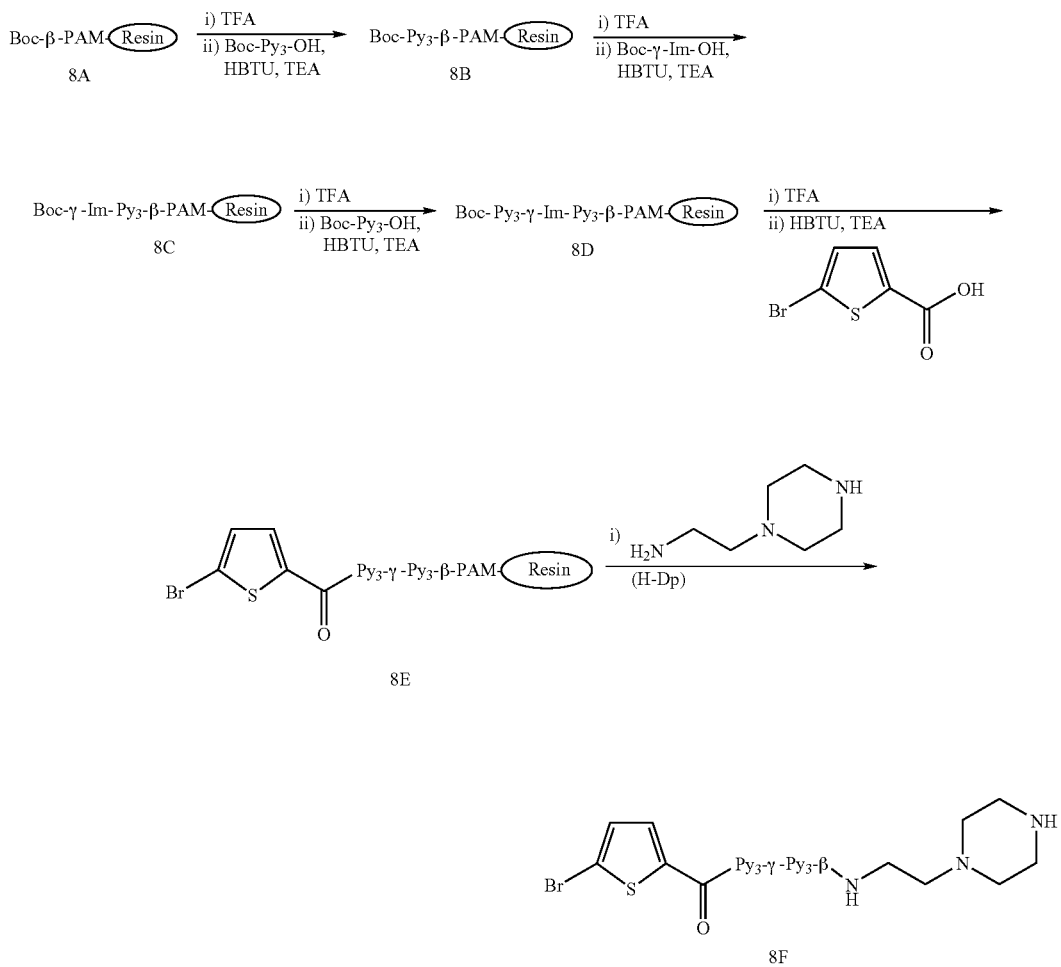

Compound If-2 (8F) was synthesized using the Argonaut Quest 210 semi-automated synthesizer as described for the synthesis of compound Id-1. In the first synthesis cycle, Boc-β-alanine-PAM resin (8A, 200 mg) was placed in a disposable vessel and manually washed with CH$_2$Cl$_2$. The protecting Boc group was then removed by manually adding 100% TFA (5 mL) and mixing for 20 minutes. The deprotected resin was washed using wash cycle B. Boc-Py$_3$-OH (166 mg, 0.34 mmol) was then activated with (121 mg, 0.34 mmol) HBTU and added to the deprotected resin in a solution NMP/TEA (2:1, 1.0 mL). The Quest 37° C. automated coupling step was used, followed by wash cycle A. The Boc-Py$_3$-β-PAM resin (8B) was then deprotected and washed as described above, after which Boc-γ-Im-OH (112 mg, 0.34 mmol) was activated with HBTU (121 mg, 0.34 mmol) and added to the deprotected resin in a solution of NMP/TEA (2:1, 1.0 mL). The Quest automated 37° C. coupling cycle was then used, followed by wash cycle A to yield the Boc-γ-Im-Py$_3$-β-alanine-PAM resin (8C). The protecting Boc group was then removed from C by manually adding 100% TFA (5 mL) and mixing for 20 minutes and washing with wash cycle B. Boc-Py$_3$-OH (166 mg, 0.34 mmol) was then activated with HBTU (121 mg, 0.34 mmol) and added to the deprotected resin in a solution NMP/TEA (2:1, 1.0 mL). The Quest 37° C. automated coupling step was used, followed by wash cycle A, yielding Boc-Py$_3$-γ-Im-Py$_3$-β-PAM resin (8D).

In the last cycle, Boc-Py$_3$-γ-Im-Py$_3$-β-PAM resin (8D) was deprotected and washed using wash cycle two. 5-Bromothiophene-2-carboxylic acid (71 mg, 0.34 mmol) was then activated with HBTU (121 mg, 0.34 mmol) in NMP/TEA (1:1, 1.0 mL) for 20 minutes, and added to the deprotected resin in a solution of NMP/TEA (2:1, 1.5 mL). The 37° C. automated coupling step was used, followed by wash cycle A and a manual wash with NMP to yield 5-bromothiophene-2-Py$_3$-γ-Im-Py$_3$-β-PAM resin (8E). The polyamide was then cleaved from the resin by adding 1-(2-aminoethyl)piperazine (3 mL) to the dried resin and heating to 55° C. for 2 hours, using the 55° C. automated cleavage cycle, then purified by reversed phase preparative HPLC to yield compound If-2 (8F), characterized by NMR.

Other compounds If such as If-1 and If-3 were made by substituting the building blocks corresponding to the appropriate Th- and N(R$^{20}$)$_2$ groups in the last coupling and cleavage steps of the above, respectively.

Synthesis of Compound Ig-1

The synthesis of compounds Ig is illustrated below with reference to compound Ig-1, summarized in Scheme 9:

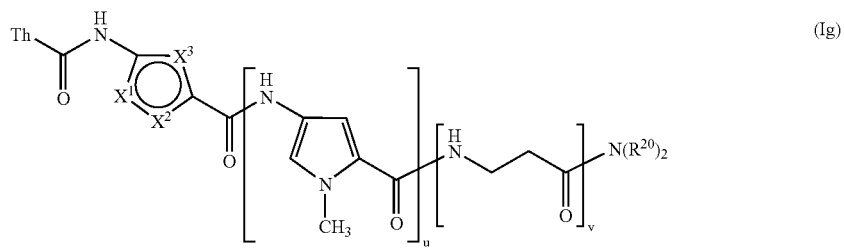
(Ig)
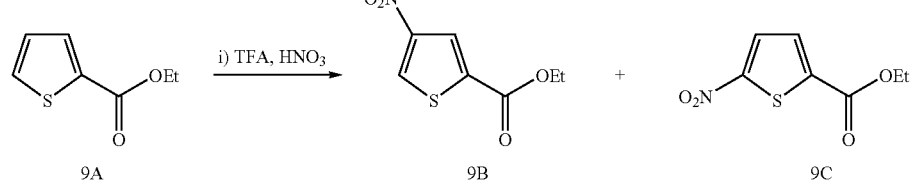
Scheme 9
Part I
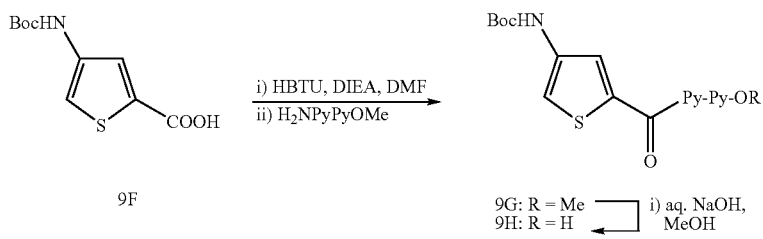
Part II

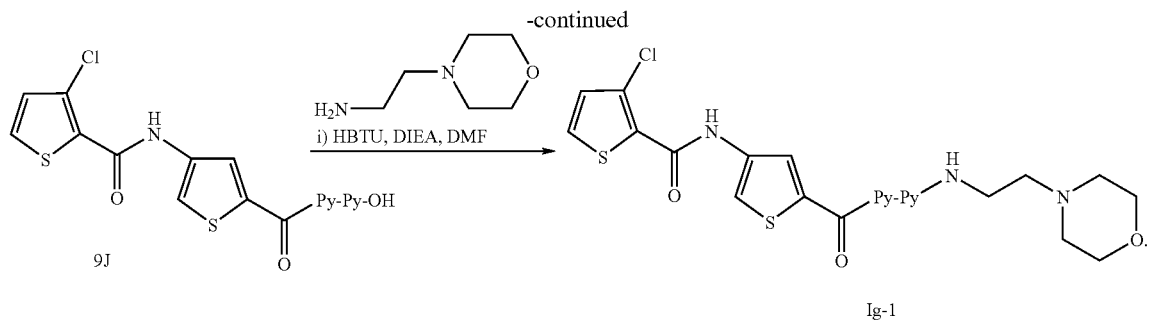

The synthesis is in two parts. In Part I, intermediate 4-Boc(amino)-2-thiophene carboxylic acid (9D) is described, while part II descirbes the synthesis of Ig-1 as a representative example.

Part I

General Description

Nitration of the thiophene ester 9A yielded a 2:3 mixture of the isomers 9B and 9C as evidenced by $^1$H-NMR (79%). Hydrogenation of this mixture followed by HCl precipitation led in good yields to the hydrochlorides 9D/9E (0.9/1, 93%). Selective saponification of the 4-aminothiophene 9D followed by Boc-protection then gave a mixture of the desired thiophene-2-carboxylic acid and 9E. At this stage, the desired acid 9F was purified by liquid/liquid extraction, avoiding flash chromatography.

Experimental

A solution of ethyl-2-thiophene carboxylate (9A, 200 g, 1 mol) in TFA (200 mL) was slowly added to a mixture of TFA (900 mL) and fuming nitric acid (200 mL) at 5° C. The cooling was removed and the reaction mixture stirred at 45° C. for ca. 14 hr, cooled to ca. 10° C., and poured into vigorously stirred ice water (4 L). The resulting precipitate was collected by filtration and washed with ice water (2×). Lyophilization of the resulting solids gave a mixture of compounds 9B/9C (2:3, as evidenced by $^1$H-NMR, 194.2 g, 79%)

A mixture of 9B/9C (2:3, 20 g) in ethyl acetate ("EtOAc," 135 mL) and methanol (15 mL) was treated with 10% Pd—C (1 g) and stirred under H$_2$ (ca. 100 psi) for 6 days at room temperature. The reaction mixture was filtered through Celite and concentrated to a volume of ca. 25 ml under reduced pressure. The residual solution was diluted with ethyl ether (500 mL), cooled to 0° C., and treated with HCl (gas) for 2 min. The resulting precipitate was collected by filtration and dried in vacuo to give a mixture of 9D/9E (0.9:1 as evidenced by $^1$H-NMR, 19.02 g, 93%).

A mixture of 9D/9E (0.9/1, 15 g) in methanol (500 mL) was treated at 0° C. with a solution of KOH (9 g) in H$_2$O (75 mL) and stirred for 3 hr. The reaction mixture was then diluted with H$_2$O (400 mL) and washed with EtOAc (3×, 200 mL). The aqueous layer was neutralized to pH=6.5 with a 1 M aq. HCl solution, treated with Na$_2$CO$_3$ (15 g) and a solution of Boc anhydride (15 g) in dioxane (150 mL) and stirred for 24 h at RT. The reaction mixture was washed with EtOAc (3×, 200 mL), cooled to 0° C., acidified to pH=2.8 with aqueous HCl (50%), and extracted with EtOAc (3×, 200 mL). The combined organic layers were dried (MgSO$_4$) and evaporated. The remaining oil was dissolved in methanol and treated with activated carbon (5 g). The mixture was filtered through Celite and the filtrate evaporated to yield 9F.

Part II

General Description

Coupling of the thiophene acid 9F to H-Py-Py-OMe gave the trimer 9G which was saponified and deprotected to give the amino acid 9I. Coupling of 3-chloro thiophene-2-carboxylic acid to 9I and subsequent activation of the product with HBTU and treatment with excess of 4-(2-aminoethyl) morpholine led to the final compound Ig-1.

Experimental

A solution of HOBt (1.51 g, 9.3 mmole, 1 eq.), DCC (2.31 g, 9.3 mmol, 1 eq.), and compound 9F (2.2 g, 9.3 mmol, 1 eq.) in DMF (15 mL) was stirred for 45 min at room temperature, treated with H-Py-Py-OMe (2.9 g, 9.3 mmol, 1 eq., Bailly et al., *J. Pharm. Sci.* November 1989, 78, 11, 910–917) and diisopropylethylamine ("DIEA") (2 mL), and stirred for 14 hr.

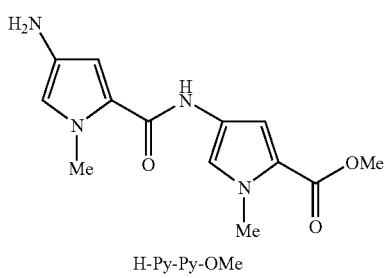

H-Py-Py-OMe

The mixture was added dropwise to ice-water (800 ml) and the resulting precipitate was collected by filtration and dried in vacuo to yield compound 9G (4.2 g).

A solution of compound 9G (2.3 g) in MeOH (20 mL) was treated with a 2 M solution of NaOH in H$_2$O (20 mL) and stirred for 3 hours at 50° C. The reaction mixture was diluted with H$_2$O and acidified to pH 2 with aqueous 1M HCl and extracted (AcOEt) three times. The combined organic layers were dried (MgSO$_4$) and evaporated to give the acid 9H (1.83 g, 83%).

The acid 9H (0.70 g) was treated with a solution of ethyl acetate (saturated with HCl, 10 ml) and stirred at 4° C. for 30 minutes. The suspension was then added dropwise into ethyl ether (400 mL), from which the solid was filtered and dried in vacuo to yield the amino acid 9I (357 mg).

A solution of 3-chlorothiophene-2-carboxylic acid (71 mg, 0.4 mmol, 1 eq.), HBTU (156 mg, 0.4 mmole, 1 eq.) in NMP (1 mL) and DIEA (0.1 mL) was stirred for 45 minutes at 37° C., treated with the amino acid 9I (140 mg, 0.4 mmol, 1 eq.), and stirred for 12 hr. The reaction mixture was added dropwise to ice water (400 mL) to form a precipitate, which was then filtered and dried in vacuo. The product compound 9J (46 mg, 0.08 mmol) was then treated with HBTU (40 mg, 0.1 mmol) in NMP (0.5 mL) and DIEA (0.05 mL) for 2 hours at room temperature, after which 4-(2-aminoethyl)morpholine (1.1 mL) was added and allowed to react for 15 hours at room temperature. The mixture was diluted with AcOH/H$_2$O, and washed with ethyl ether (3×). HPLC purification of the aqueous phase gave compound Ig-1.

Other compounds Ig can be made analogously, for example using a building block based on 4-amino-2-pyrrole carboxylic acid, whose synthesis is described in Bremer et al., *Bioorg. Med. Chem.*, 8, 1947–1955 (2000).

Alternative Synthesis of Compound Ie-6

Scheme 10 illustrates an alternative synthesis of compound Ie-6 and other compounds sharing the same general structural motif. Briefly, a three aromatic ring fragment representing the left-hand side of the molecule is synthesized and couple with a second fragment comprising a fourth aromatic ring and a group —N(R$^{20}$)$_2$. Using this method, compound Ie-6 was synthesized in high yield and purity without the need to resort to HPLC purification. Part I shows the synthesis of the three ring fragment 10H.

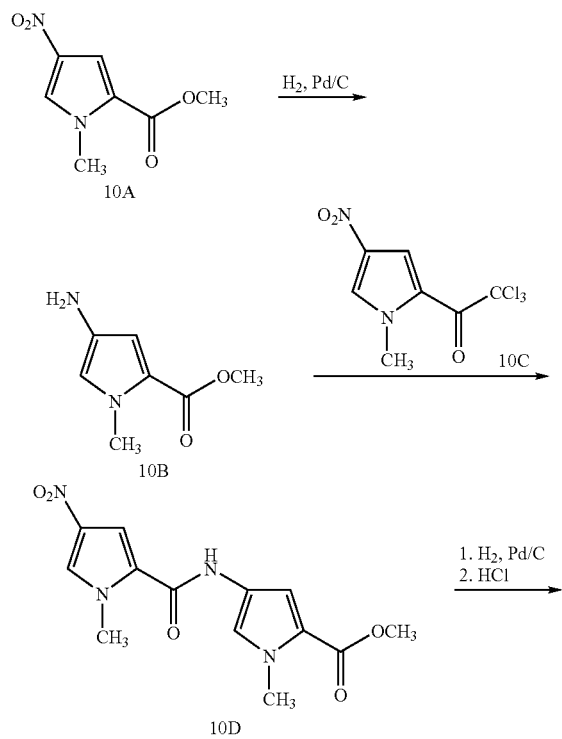

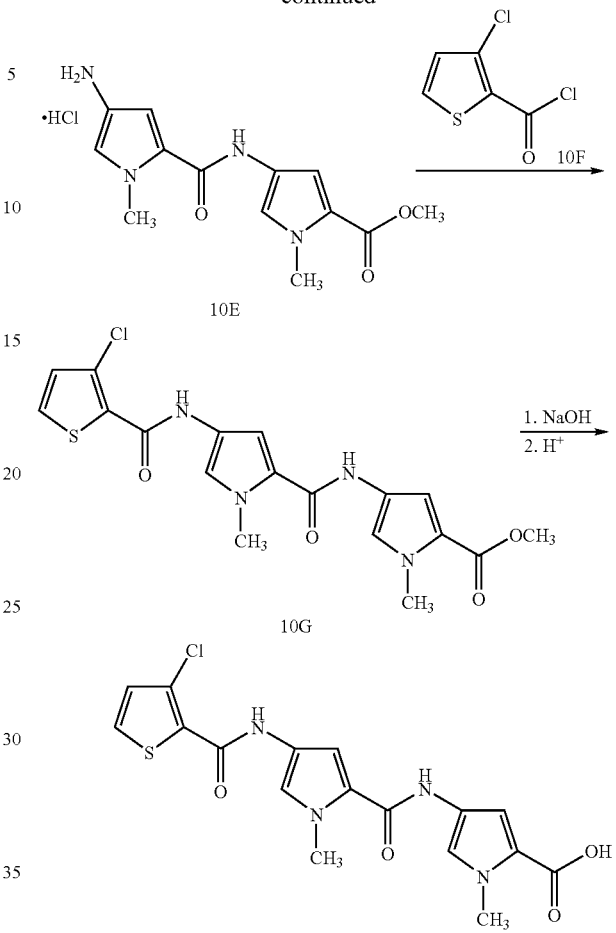

Synthesis of nitro ester 10D. Pd/C (10%) (5 g) was added into a solution of compound 10A (100 g, 0.543 mole) in THF (1L) in a 2L autoclave under N$_2$. The autoclave was then degassed under vacuum. H$_2$ was passed into the autoclave and the reaction was allowed to proceed at 125 psi at room temperature. After stirring for 2 hr, the reaction was determined to be complete by TLC (Toluene:EtOAc=7:3 (v/v), R$_f$=0.85). The reaction mixture was filtered through a Celite cake and concentrated in vacuo. Then, DMF (220 mL) was added to dissolve the resulting compound 10B before compound 10C (147.3 g, 0.542 mole) was added. After 5 min the exothermic reaction mixture became thicker and then became almost solid. After the reaction mixture was cooled to room temperature, THF (1 L) was added and the solid was grounded into powder. Pure product 10D (126.7 g, 0.414 mole, 76.2% yield for 2 steps) was obtained after filtration, washing with diethyl ether, and drying.

Synthesis of amino ester 10E. Pd/C (10%) (1.5 g) was added into a solution of nitro ester 10D (30 g, 0.098 mole) in MeOH (750 mL) in a 2L autoclave under N$_2$. The autoclave was then degassed under vacuum. H$_2$ was passed into the autoclave and the reaction was allowed to proceed at 125 psi at 60° C. After stirring at 60° C. for 2 hr, the reaction was determined to be complete by TLC (Toluene:EtOAc=8:2 (v/v), R$_f$=0.53). The reaction mixture was cooled to room temperature and filtered through a Celite cake. After evaporating off the MeOH, 2 L Et$_2$O (anhydrous) was added to the reaction mixture and HCl(gas) was passed through the solution. Pure product 10E (29.1 g, 0.093 mole, 94% yield) was obtained after filtration, washing with diethyl ether (3×50 mL) and dried under vacuum.

Synthesis of acid 10H. DIEA (30 g, 0.232 mole) was added into a suspension of amino ester 10E (as hydrochloride, 31 g, 0.099 mole) in DMF(600 mL) in a 1 L round-bottomed flask while stirring at room temperature. The mixture became clear. Acid chloride 10F (21 g, 0.116 mole, 1.2 equiv) was added to the reaction mixture with stirring at room temperature. After 3 hr., the reaction was determined to be complete by TLC. The reaction mixture was poured into 1200 mL ice water under vigorous stirring. The solid (crude ester 10G) was collected by filtration and washed with water (3×200 mL). The resulting solid 10G was added to a solution of NaOH (2N, 200 mL) in MeOH (200 mL) and heated at 50° C. overnight (12 hr). After confirming the completion of the reaction by TLC, the aqueous reaction mixture was extracted/washed with diethyl ether (3×50 mL) and acidified to PH 3 (10% H$_2$SO$_4$). The resulting precipitate was filtered, re-crystallized from MeOH (500 mL) to obtain a pure product acid 101H (30 g, 0.074 mole, 75% yield for 2 steps).

Part II shows the synthesis of the right-hand fragment 10J and its coupling to the left-hand fragment 10H to make compound Ie-6.

Synthesis of nitro compound 10I. 1-Methyl-2-trichloroacetyl-4-nitropyrrole 10C (135.2 g, 0.498 mole) was added into the solution of 1208 (65 g, 0.499 mole) in THF (600 mL) in a 1 L three-necked round-bottomed flask while stirring at room temperature. The reaction was exothermic, and the reaction temperature reached 50° C. in 3 min. The reaction was completed in 2 hr, as indicated by TLC [CH$_2$Cl$_2$:MeOH (v/v)=9:1]. The reaction mixture was concentrated in vacuo to remove THF and triturated with ether (300 mL). The resulting solid was filtered, washed with ether, and dried to afford crude compound 10I as a light yellow solid (136 g, 0.482 mole, 96.5% yield). Crude compound 10I (68 g) was dissolved in 400 ml dry EtOAc under reflux. The resulting solution was then cooled to 0° C. for 4 h. After filtration and drying under high vacuum, the pure nitro compound 10I (62 g, 88% yield) was obtained.

Synthesis of amine 10J. Pd/C (10%) (2.5 g) was added into a solution of nitro compound 10I (50 g, 0.177 mole) in THF (500 mL) in a 2L autoclave under N$_2$. The autoclave was de-gassed under vacuum. H$_2$ was passed into the autoclave and the reaction was allowed to proceed at 125 psi at room temperature. After stirring for 2 h, the reaction was complete, as indicated by TLC (Toluene:EtOAc=7:3 (v/v), R$_f$=0.85). The reaction mixture was filtered through a celite cake, diluted with anhydrous ether (2L). HCl (gas) was passed through the reaction mixture to precipitate out compound 10J as the hydrochloride. Pure compound 10J (48 g, 0.166 mole, 94% yield) was obtained after filtration and washing with diethyl ether (3×50 mL) and drying under vacuum.

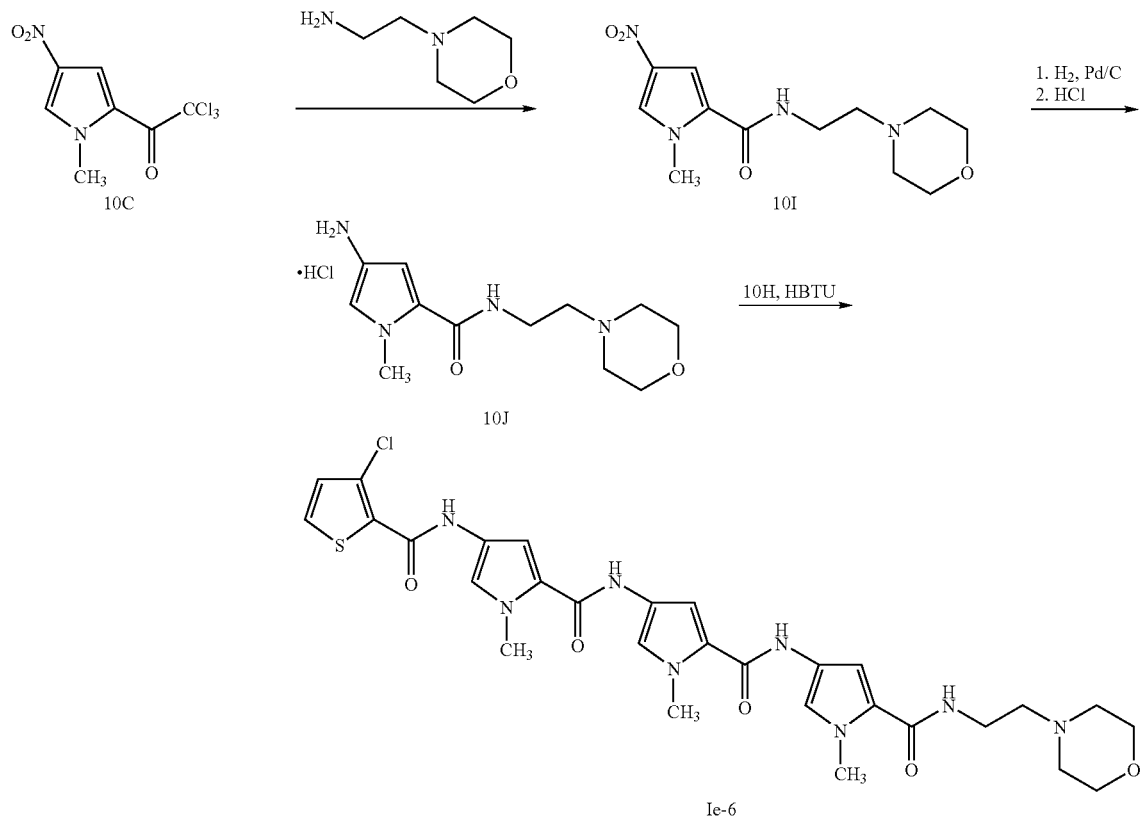

Scheme 10 (Part II)

Ie-6

Synthesis of compound Ie-6 by coupling of compounds 10H and 10. DIEA(23 g, 0.178 mole) was added into a solution of compound 10H (30 g, 0.074 mole) and HBTU (32 g, 0.084 mole) in DMF (500 mL) in a 1 L round bottom flask while stirring at room temperature. The reaction mixture was stirred at 45° C. for 30 min. Then compound 10J (26 g, 0.090 mole, 1.2 eq) was added into the reaction mixture and stirred at 50° C. After 15 hr, the reaction was complete, as indicated by TLC. The reaction mixture was cooled to room temperature and poured into 1.5 L ice water under vigorous stirring. The resulting precipitate was filtered, purified by silica gel flash chromatography (eluent MeOH/CH2Cl2=1:9 (v/v)) to afford the compound Ie-6 (31 g, 0.048 mole, 65.5% yield). Compound Ie-6 could be recrystallized as follows: compound Ie-6 (16.5 g) was dissolved in EtOH/CH2Cl2 (300 mL/200 mL) at 40° C. After the solution was cooled to room temperature and evaporated slowly to 300 mL, product was crystallized out. The pure product Ie-6 (14.3 g, 87% yield) was obtained after filtration, washing with cold ethanol and drying in vacuum.

Biological Activity

Compounds according to this invention were screened for their in vitro activities against selected species of bacteria and fungi. The minimal inhibition concentration (MIC) of these compounds was determined using the National Committee for Clinical Laboratory Standards (NCCLS) broth microdilution assay in microtiter plates, as set forth in: (1) the guidelines of the National Committee for Clinical Laboratory Standards (NCCLS) Document M7-A4 (NCCLS, 1997); (2) the guidelines of the National Committee for Clinical Laboratory Standards (NCCLS) Document M11-A4 (NCCLS, 1997); and (3) the guidelines and reference method of the National Committee for Clinical Laboratory Standards (NCCLS) Document M27-T (NCCLS, 1995). For antifungal essays, the method recommended in Murray, PR., 1995 *Manual of Clinical Microbiology* (ASM Press, Washington, D.C.), was employed. The results are presented in Table IV below. (Data for distamycin, netropsin, and ofloxacin are comparative.). The data in Table IV is keyed as follows:

TABLE IV

Biological Activity

Organism (Minimum Inhibitory Concentration (MIC), μg/mL)

| Compound | A | B | C | D | E | F |
|---|---|---|---|---|---|---|
| If-2 | >32 | >32 | >32 | >32 | >32 | >32 |
| If-1 | >32 | >32 | >32 | >32 | >32 | >32 |
| Id-1 | +++ | +++ | +++ | >32 | >32 | +++ |
| Id-2 | +++ | +++ | +++ | >32 | >32 | +++ |
| Id-3 | +++ | +++ | +++ | >32 | >32 | +++ |
| Id-4 | +++ | +++ | +++ | >32 | >32 | +++ |
| Id-5 | +++ | +++ | +++ | >32 | >32 | +++ |
| Id-6 | +++ | +++ | +++ | >32 | >32 | +++ |
| Id-15 | >32 | + | + | ND | >32 | ++ |
| Id-16 | >32 | >32 | >32 | >32 | >32 | +++ |
| Id-17 | + | ++ | +++ | >32 | >32 | +++ |
| Id-18 | >32 | ++ | + | >32 | >32 | +++ |
| Id-19 | >32 | +++ | +++ | >32 | >32 | +++ |
| Id-20 | >32 | >32 | >32 | >32 | >32 | +++ |
| Id-21 | >32 | +++ | +++ | >32 | >32 | +++ |
| Id-7 | +++ | +++ | +++ | >32 | >32 | +++ |

TABLE IV-continued

Biological Activity

Organism (Minimum Inhibitory Concentration (MIC), μg/mL)

| Compound | A | B | C | D | E | F |
|---|---|---|---|---|---|---|
| Id-22 | >32 | +++ | +++ | >32 | >32 | +++ |
| Id-8 | >32 | +++ | >32 | >32 | >32 | +++ |
| Id-23 | >32 | +++ | >32 | >32 | >32 | +++ |
| Id-9 | +++ | +++ | +++ | >32 | >32 | +++ |
| Id-25 | + | + | +++ | >32 | >32 | +++ |
| Id-10 | >32 | >32 | >32 | >32 | >32 | +++ |
| Id-30 | >32 | >32 | >32 | >32 | >32 | ++ |
| Ie-4 | ++ | ++ | + | >32 | >32 | +++ |
| Ie-5 | +++ | >32 | +++ | >32 | >32 | +++ |
| Ie-3 | ++ | >32 | ND | ND | >32 | +++ |
| Ie-11 | +++ | +++ | +++ | >32 | >32 | +++ |
| Ie-12 | ND | +++ | +++ | >32 | >32 | +++ |
| Ie-13 | ND | +++ | +++ | >32 | >32 | +++ |
| Ie-14 | ND | +++ | +++ | >32 | >32 | +++ |
| Ie-15 | ND | +++ | +++ | + | + | +++ |
| Id-12 | +++ | +++ | +++ | >32 | >32 | +++ |
| Id-13 | >32 | >32 | >32 | >32 | >32 | >32 |
| Id-27 | ++ | >32 | +++ | >32 | + | +++ |
| Ie-6 | +++ | +++ | +++ | >32 | >32 | +++ |
| Ie-2 | +++ | +++ | ND | ND | >32 | +++ |
| Id-26 | >32 | >32 | ND | ND | >32 | + |
| Id-29 | >32 | >32 | ND | ND | >32 | >32 |
| Id-28 | +++ | + | ND | ND | >32 | +++ |
| Ig-1 | +++ | +++ | ND | ND | >32 | ++ |
| Ig-2 | >32 | >32 | ND | ND | >32 | >32 |
| Ig-4 | +++ | +++ | ND | ND | >32 | +++ |
| Ig-5 | +++ | +++ | ND | ND | >32 | +++ |
| Ig-10 | ND | +++ | +++ | >32 | >32 | +++ |
| Ih-2 | ND | +++ | >32 | >32 | >32 | +++ |
| Distamycin | + | + | ++ | >32 | >32 | + |
| Netropsin | +++ | +++ | +++ | +++ | — | +++ |
| Ofloxacin | +++ | ++ | +++ | +++ | — | +++ |

Key:
+++ = MIC ≤ 4
++ = MIC between 4 and 12
+ = MIC from 12 to 32, inclusive
ND = No data available
>32 = preliminary data indicates MIC greater than 32
A = *S. aureus* ATCC 29213
B = *E. faecalis* ATCC 29212
C = *B. cereus* ATCC 11778
D = *E. coli* ATCC 25922
E = *C. albicans* ATCC 38247
F = *S. pneumoniae* ATCC 49619

The activity against Gram-positive bacteria (e.g., *Staphylococcus aureus* (ATCC29213), *Bacillus cereus* (ATCC 11778), *Enterococcus faecalis* (ATCC 29212), *Streptococcus pneumoniae* (ATCC 49619)) is noteworthy. Preferably, compounds of this invention have an MIC of 8 μg/mL or less against at least two of the aforementioned Gram-positive bacteria strains, and more preferably an MIC of 1 μg/mL or less against at least two of them.

DNA Binding

A number of compounds according to this invention were screened for their ability to bind to three DNA sites, using DNase I footprinting. Generally, the procedure described in Dervan, WO 98/50582 (1998), was followed.

A plasmid was prepared by hybridizing two sets of 5'-phosphorylated complementary oligonucleotides, one set being 5'-CCGGGAACGTAGCGTACCGGTGC
AAAAAGCAAAAAGGCTCGACGCCGC
AAAAAGACAAAAAGGCTCGA-3' (SEQ ID NO:1)

and

5'-GGCGTCGAGCC
TTTTTGTCTTTTTGCGGCGTCGAGCC
TTTTTGCTTTTTGCACCGGTACGCTACGTTC-3'
(SEQ ID NO:2)

and the other set being

5'-CGCCGCAAAAAGTACAAAAAGGCTCGACGC-
CGCAGCTCGTCCTAGCTAGCGTCGTAGCGTC-
TTAAG-3' (SEQ ID NO:3)

and

5'-TCGACTTAAGACGCTACGACGCTAGCTAG-
GACGAGCTGCGGCGTCGAGCCTTTTTGTA-
CTTTTTGC-3' (SEQ ID NO:4)

The target sites and their complements are identified in bold underline.

The resulting duplexes were ligated to the large pUC19 AvaI/SalI restriction fragment. The 3'-P32 end-labeled EcoRI/PvuII fragment was prepared by digesting the plasmid with EcoRI and PvuII with simultaneous fill-in using Sequenase v. 2.0, [alpha-P32]-deoxyadenosine-5'-triphosphate, and [alpha-P32]-thymidine-5'-triphosphate, and isolating the cloned fragment by nondenaturing gel electrophoresis. Standard methods were used for all DNA manipulations, including A and G sequencing. See, e.g., Maxam et al., *Methods Enzymol.*, 1980, 65, 499–560; Iverson et al., *Methods Enzymol.*, 1987, 15, 7823–7830; and Sambrook et al., 1989, *Molecular Cloning*, $2^{nd}$ ed., Cold Spring Harbor Laboratory Press: Cold Spring Harbor, N.Y.

Quantitative DNase I footprint titration experiments were carried out as described previously (Dervan, WO 98/50582, 1998, "Dervan '582") with the following changes. All reactions were carried out in a total volume of 400 μL, with polyamide stock solution or water added to 15,000 cpm radiolabeled restriction fragment affording final solution conditions of 10 mM Tris•HCl, 10 mM KCl, 10 mM $MgCl_2$, 5 mM $CaCl_2$, pH 7.0 and 0.01 nM, 0.1 nM, 1.0 nM, 10.0 nM polyamide or no polyamide for reference lanes. The polyamides were allowed to equilibrate at 22° C. for 16 hr. Footprinting reactions were initiated with addition of 10 μL of a DNase I stock solution (at the appropriate concentration to give ~50% intact DNA) containing 1 mM DTT and allowed to proceed for 7 min at 22° C. The reactions were stopped, ethanol precipitated, resuspended in loading buffer, heat denatured, and placed on ice as described in Dervan '582. The reaction products were separated on a precast 8% polyacrylamide denaturing sequencing Castaway gel with 32 preformed wells from Stratagene in 1×TBE at 2000 V. Gels were dried according to the manufacturer's instructions and exposed to a storage phosphor screen (Molecular Dynamics). Quantitation and data analysis were carried out as described in Dervan '582.

The results are presented in Table V below:

TABLE V

DNA Binding

DNA Sequence and Equilibrium Association Constant ($K_a$, $M^{-1}$)

| Compound ID | 5'-AAAAAGCAAAAA-3' (SEQ ID NO:5) | 5'-AAAAAGACAAAAA-3' (SEQ ID NO:6) | 5'-AAAAAGTACAAAAA-3' (SEQ ID NO:7) |
|---|---|---|---|
| Id-1  | $\geq 1 \times 10^{11}$ | $\geq 1 \times 10^{11}$ | $\geq 1 \times 10^{11}$ |
| Id-2  | $5 \times 10^{8}$       | $5 \times 10^{8}$       | $5 \times 10^{9}$ |
| Id-3  | $5 \times 10^{8}$       | $5 \times 10^{8}$       | $5 \times 10^{9}$ |
| Id-4  | $5 \times 10^{9}$       | $1 \times 10^{10}$      | $5 \times 10^{11}$ |
| Id-5  | $2 \times 10^{9}$       | $2 \times 10^{10}$      | $1 \times 10^{11}$ |
| Id-6  | $1 \times 10^{10}$      | $1 \times 10^{10}$      | $\geq 1 \times 10^{11}$ |
| Id-15 | $5 \times 10^{10}$      | $5 \times 10^{10}$      | $\geq 1 \times 10^{11}$ |
| Id-16 | $5 \times 10^{10}$      | $5 \times 10^{10}$      | $\geq 1 \times 10^{11}$ |
| Id-17 | $\geq 1 \times 10^{11}$ | $\geq 1 \times 10^{11}$ | $\geq 1 \times 10^{11}$ |
| Id-18 | $\geq 1 \times 10^{11}$ | $\geq 1 \times 10^{11}$ | $\geq 1 \times 10^{11}$ |
| Id-19 | $5 \times 10^{9}$       | $5 \times 10^{9}$       | $\geq 1 \times 10^{11}$ |
| Id-21 | $5 \times 10^{10}$      | $1 \times 10^{10}$      | $\geq 1 \times 10^{11}$ |
| Id-7  | $5 \times 10^{8}$       | $5 \times 10^{8}$       | $\geq 1 \times 10^{11}$ |
| Id-22 | $2 \times 10^{8}$       | $2 \times 10^{8}$       | $\geq 1 \times 10^{11}$ |

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various descriptions herein relate to specific embodiments of the invention, it is to be understood that where a specific feature is disclosed in the context of a particular embodiment, such feature can also be used, to the extent appropriate, in the context of another embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. A thienyl compound having formula $$Th-(D^1)-(Y)_m-B^5(R^{20})_p$$

and the pharmaceutically acid addition salts thereof, wherein

Th is

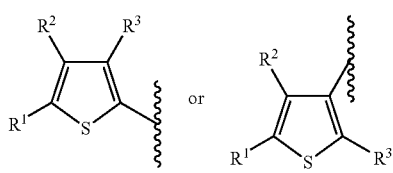

or wherein each of $R^1$, $R^2$, and $R^3$ is H, F, Cl, Br, I, OH, $NO_2$, a substituted or unsubstituted $(C_1-C_{12})$alkyl group, or a substituted or unsubstituted $(C_1-C_{12})$ heteroalkyl group; with the provisos that, when m is 3 or greater, at least one of $R^1$, $R^2$, and $R^3$ is F, Cl, Br or I and that, when m is 2, at least one of $R^2$ and $R^3$ is F, Cl, Br, or I, but $R^1$, $R^2$, and $R^3$ being otherwise independently variable;

$D^1$ is selected from the group consisting of a chemical bond, a substituted or unsubstituted $(C_1-C_6)$alkylene group, —S(=O)—, and —S(=O)$_2$—;

m is an integer ranging from 2 to 25, inclusive;

each Y is independently selected from the group consisting of (a) moieties $M^1$ having the formula

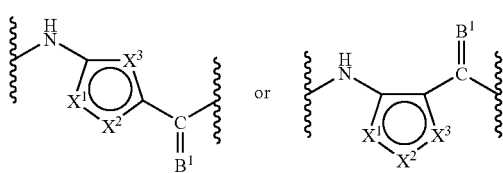

wherein
each $B^1$ is independently selected from O, S, or NH;
one of $X_1$, $X_2$, and $X_3$ is a ring vertex selected from the group consisting of —O—, —S—, and —$NR^{10}$—, and the other two of $X_1$, $X_2$, and $X_3$ are ring vertices selected from the group consisting of =N— and =$CR^{11}$—;
each $R^{10}$ is independently H, a substituted or unsubstituted ($C_1$–$C_{12}$)alkyl group, or a substituted or unsubstituted ($C_1$–$C_{12}$)heteroalkyl group; and
each $R^{11}$ is independently H, Cl, F, Br, I, OH, $NO_2$, a substituted or unsubstituted ($C_1$–$C_{12}$)alkyl group, or a substituted or unsubstituted ($C_1$–$C_{12}$)heteroalkyl group;

(b) moieties $M^2$ having the formula

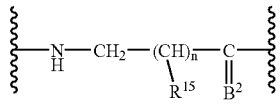

wherein
n is 0 or 1;
each $B^2$ is independently O, S, or NH; and
each $R^{15}$ is independently H, OH, $NH_2$, or F; and (c) moieties $M^3$ having the formula

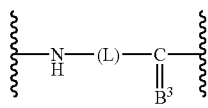

wherein
each $B^3$ is independently O, S, or NH and
each L is independently a divalent moiety separating —NH— and —(C=$B^3$)— by 3 or 4 atoms;
$B^5$ is N or O;
p is 1 if $B^5$ is O and 2 if $B^5$ is N; and
each $R^{20}$ is independently H, a substituted or unsubstituted ($C_1$–$C_{12}$)alkyl group or a substituted or unsubstituted ($C_1$–$C_{12}$)heteroalkyl group;
with the proviso that at least one of $R^1$, $R^2$, $R^3$, $R^{10}$, $R^{11}$, and $R^{20}$ contains at least one basic group having a $pK_b$ of 12 or less and that at least two Y's are moieties $M^1$.

2. A thienyl compound according to claim 1, wherein $D^1$ is —C(=O)— and wherein at least two moieties $M^1$ are selected from the group consisting of

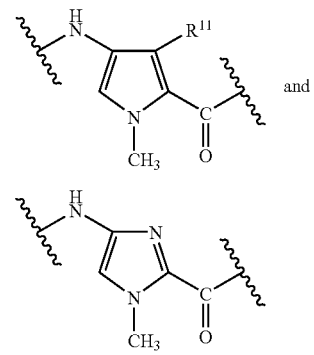

wherein $R^{11}$ is H or OH.

3. A thienyl compound according to claim 1, having a moiety $M^2$ having the formula

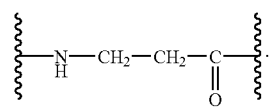

4. A thienyl compound according to claim 1, wherein $R^1$ is other than F, Cl, Br, or I.

5. A thienyl compound according to claim 1, wherein $B^5$ is N and at least one group $R^{20}$ has a basic group having a $pK_b$ of 12 or less.

6. A thienyl compound according to claim 1, wherein the basic group having a $pK_b$ of 12 or less is a primary, secondary, or tertiary alkyl amine, a guanidine, or an amidine.

7. A thienyl compound according to claim 1, having a moiety $M^3$ selected from the group consisting of

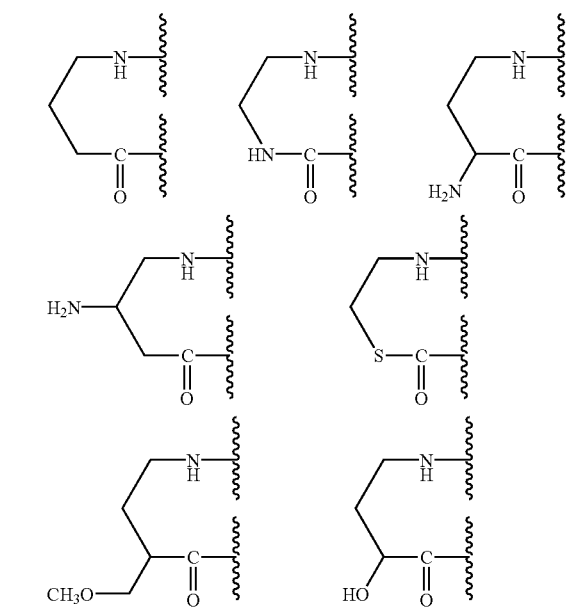

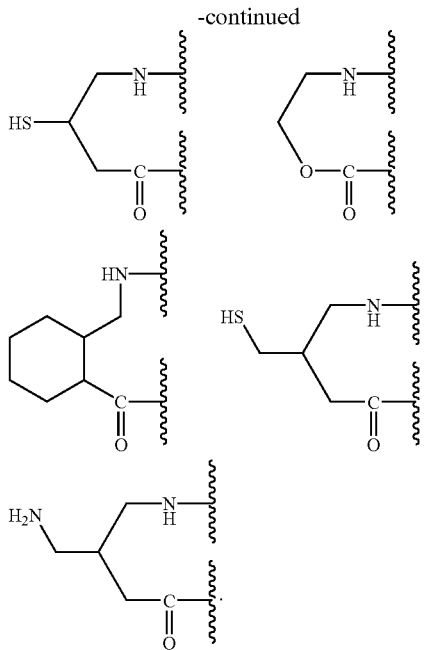

8. A thienyl compound according to claim 1, having the formula

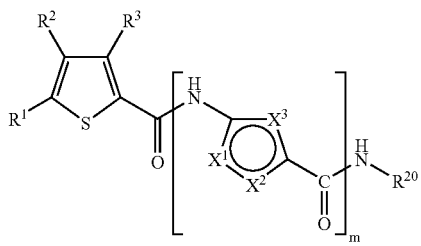

wherein m is 2, 3, 4, or 5.

9. A thienyl compound according to claim 8, wherein $R^1$ is other than F, Cl, Br, or I.

10. A thienyl compound according to claim 8, wherein m is 3 or 4.

11. A thienyl compound according to claim 8, wherein $R^3$ is Cl.

12. A thienyl compound according to claim 11, wherein $R^1$ is H and $R^2$ is Br.

13. A thienyl compound according to claim 11, wherein $R^1$ and $R^2$ are both H.

14. A thienyl compound according to claim 11, wherein $R^1$ is H and $R^2$ is $CH_3$.

15. A thienyl compound according to claim 8, wherein each

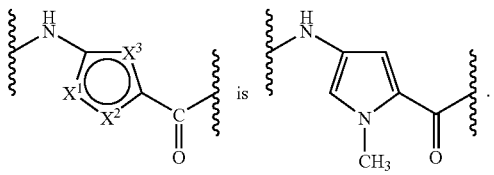 is 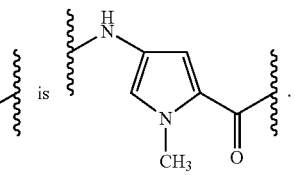.

16. A thienyl compound according to claim 8, wherein the basic group having a $pK_b$ of 12 or less is a primary, secondary, or tertiary alkyl amine, a guanidine, or an amidine.

17. A thienyl compound according to claim 8, wherein the residue $NHR^{20}$ is selected from the group consisting of

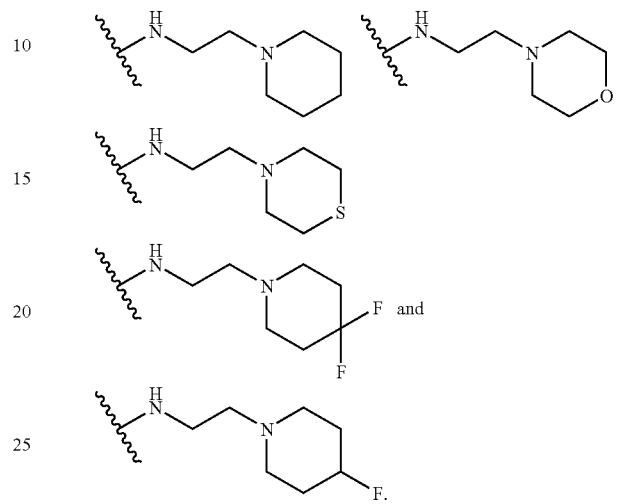

18. A thienyl compound according to claim 1, having the formula

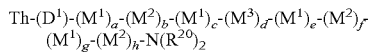

wherein each of a, c, e, g, and h is an integer independently ranging from 0 to 5, inclusive, and each of b, d, and f is independently 0 or 1; with the proviso that the sum of a, c, e, and g is at least 3.

19. A thienyl compound according to claim 18, wherein $D^1$ is —C(=O)—.

20. A thienyl compound according to claim 18, wherein at least one of b, f, and h is 1 and moiety $M^2$ has the formula

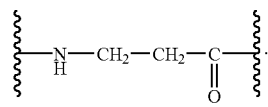

21. A thienyl compound according to claim 18, wherein d is 1 and moiety $M^3$ has the formula

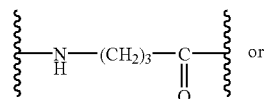 or

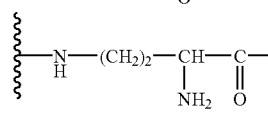

22. A thienyl compound according to claim 18, wherein at least one group $R^{20}$ has a basic group having a $pK_b$ of 12 or less.

23. A thienyl compound according to claim 1, having the formula

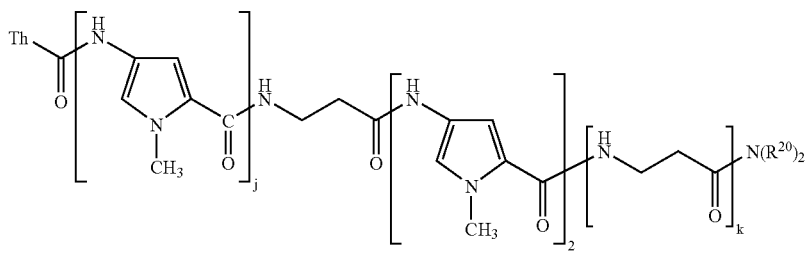

wherein j is 1 or 2, k is 0 or 1, and $N(R^{20})_2$ has a basic group having a $pK_b$ of 12 or less.

24. A thienyl compound according to claim 1, having the formula

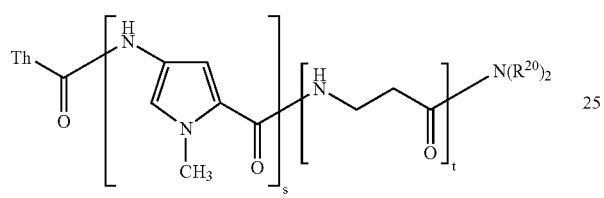

wherein s is 3 or 4, t is 0 or 1, and $N(R^{20})_2$ has a basic group having a $pK_b$ of 12 or less.

25. A thienyl compound according to claim 1, having the formula

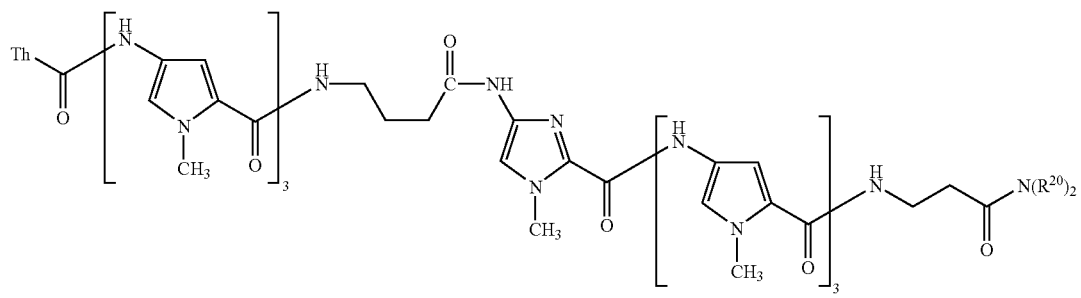

wherein $N(R^{20})_2$ has a basic group having a $pK_b$ of 12 or less.

26. A thienyl compound according to claim 1, having the formula

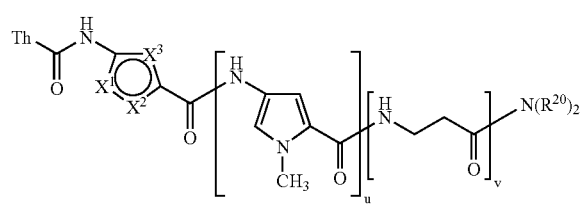

wherein u is 2, v is 0 or 1, and $N(R^{20})_2$ has a basic group having a $pK_b$ of 12 or less.

27. A method of treating an infection in an eukaryotic organism by a Gram-positive bacteria, comprising administering to the eukaryotic organism an effective amount of a thienyl compound according to claim 1.

28. A method according to claim 27, wherein the eukaryotic organism is a human.

* * * * *

UNITED STATES PATENT AND TRADEMARK OFFICE
CERTIFICATE OF CORRECTION

PATENT NO. : 7,122,626 B2 Page 1 of 1
APPLICATION NO. : 10/132887
DATED : October 17, 2006
INVENTOR(S) : Yigong Ge et al.

It is certified that error appears in the above-identified patent and that said Letters Patent is hereby corrected as shown below:

On the Title Pg, Item (73) Assignee:

change "GeneSoft Pharmceuticals, Inc." to --GeneSoft Pharmaceuticals, Inc.--

Signed and Sealed this

Twenty-ninth Day of May, 2007

JON W. DUDAS
*Director of the United States Patent and Trademark Office*